United States Patent
Starzl et al.

[11] Patent Number: 5,958,704
[45] Date of Patent: Sep. 28, 1999

[54] SENSING SYSTEM FOR SPECIFIC SUBSTANCE AND MOLECULE DETECTION

[75] Inventors: Timothy W. Starzl, Boulder; David W. Nunnery, Westminster; MaryBeth Robinson, Boulder; H. John Hanlin, Louisville, all of Colo.

[73] Assignee: DDx, Inc., Denver, Colo.

[21] Appl. No.: 08/820,365

[22] Filed: Mar. 12, 1997

[51] Int. Cl.⁶ .................... G01N 33/53; G01N 33/543
[52] U.S. Cl. .............. 435/7.1; 422/55; 422/57; 422/58; 422/63; 422/65; 422/66; 422/67; 422/82.05; 435/287.1; 435/287.2; 435/288.7; 435/808; 436/47; 436/164; 436/518; 436/524; 436/805; 356/364; 356/369
[58] Field of Search .................. 422/55, 57, 58, 422/82.05, 63, 66, 65, 67; 435/287.1, 287.2, 288.7, 808, 7.1; 436/47, 51 B, 524, 805, 164; 356/364, 369

[56] References Cited

U.S. PATENT DOCUMENTS

| | | | |
|---|---|---|---|
| Re. 31,712 | 10/1984 | Giese | 428/407 |
| Re. 33,581 | 4/1991 | Nicoli et al. | 435/7.2 |
| 2,666,355 | 1/1954 | Trurnit | 88/14 |
| 3,904,293 | 9/1975 | Gee | 356/118 |
| 3,926,564 | 12/1975 | Giaever | 23/259 |
| 4,224,439 | 9/1980 | Ayers et al. | 536/32 |
| 4,233,847 | 11/1980 | Walker | 73/517 R |
| 4,282,287 | 8/1981 | Giese | 428/407 |
| 4,330,440 | 5/1982 | Ayers et al. | 525/54.31 |
| 4,332,476 | 6/1982 | Stenberg et al. | 356/369 |
| 4,357,142 | 11/1982 | Schall, Jr. et al. | 23/230 B |
| 4,363,634 | 12/1982 | Schall, Jr. | 23/230 B |
| 4,390,343 | 6/1983 | Walter | 436/518 |
| 4,478,914 | 10/1984 | Giese | 428/407 |
| 4,508,832 | 4/1985 | Carter et al. | 436/517 |
| 4,521,522 | 6/1985 | Lundström et al. | 436/525 |
| 4,558,012 | 12/1985 | Nygren et al. | 436/501 |
| 4,588,624 | 5/1986 | Nygren et al. | 428/36 |
| 4,613,567 | 9/1986 | Yasoshima et al. | 435/7 |
| 4,655,595 | 4/1987 | Björk et al. | 356/369 |

(List continued on next page.)

OTHER PUBLICATIONS

K.M. Johnson et, (1987), *Optical Engineering*, 26(5):385–391.

*Primary Examiner*—Christopher L. Chin
*Attorney, Agent, or Firm*—Sheridan Ross P.C.

[57] ABSTRACT

A system for detecting a specific substance or analyte of interest is provided that includes one or more sensing units and an instrument for analyzing the sensing units. Each sensing unit preferably includes a substrate, an attachment layer and at least one capture layer that includes a ligand layer. In one embodiment, the attachment layer is tripartite and includes a lower binding surface held to the substrate and an upper binding surface that holds the ligand layer, together with an insulating layer disposed between these two surfaces. The lower binding surface provides a durable and stable attachment to the substrate. The upper binding surface holds the ligand layer and does not jeopardize the integrity or viability thereof. The insulating layer prevents any unwanted interaction between the lower and upper binding surfaces. Each sensing unit is supported on a test piece received by the instrument. The instrument controllably positions the test piece using marks and/or codes on the test piece. The instrument measures a difference in mass in the sensing unit in connection with determining whether or not the analyte of interest is present. A light beam is used in making this measurement. In one embodiment, multiple reflections of the light beam on the same sensing unit are utilized to improve the sensitivity of the instrument. Mass enhancement techniques are also preferably utilized to effectively amplify the detected signal that is indicative of the analyte's presence. The system can also include a device for heating, humidifying and mixing materials of the sensing units, as well as preventing cross-contamination of the sensing units.

23 Claims, 22 Drawing Sheets

U.S. PATENT DOCUMENTS

| | | | |
|---|---|---|---|
| 4,668,584 | 5/1987 | Uzgiris et al. | 428/408 |
| 4,672,024 | 6/1987 | Giaever et al. | 430/396 |
| 4,673,584 | 6/1987 | Nygren et al. | 427/2 |
| 4,713,350 | 12/1987 | Siegel et al. | 436/533 |
| 4,748,329 | 5/1988 | Cielo et al. | 250/560 |
| 4,767,719 | 8/1988 | Finlan | 436/501 |
| 4,794,090 | 12/1988 | Parham et al. | 436/531 |
| 4,801,798 | 1/1989 | Lange | 250/225 |
| 4,820,649 | 4/1989 | Kawaguchi et al. | 436/501 |
| 4,829,009 | 5/1989 | Graves | 436/518 |
| 4,849,458 | 7/1989 | Reed et al. | 521/159 |
| 4,880,798 | 11/1989 | Kato et al. | 514/206 |
| 4,902,134 | 2/1990 | Spanier | 356/364 |
| 4,931,384 | 6/1990 | Layton et al. | 435/7 |
| 4,957,368 | 9/1990 | Smith | 356/369 |
| 4,978,724 | 12/1990 | Clark | 525/350 |
| 4,978,732 | 12/1990 | Wehrmann et al. | 528/71 |
| 4,980,278 | 12/1990 | Yamada et al. | 435/7 |
| 4,992,385 | 2/1991 | Godfrey | 436/525 |
| 5,028,335 | 7/1991 | Sleytr et al. | 210/638 |
| 5,034,330 | 7/1991 | Yamori et al. | 435/288 |
| 5,037,737 | 8/1991 | Liffmann et al. | 435/11 |
| 5,061,072 | 10/1991 | Folkard et al. | 356/369 |
| 5,089,387 | 2/1992 | Tsay et al. | 435/6 |
| 5,091,206 | 2/1992 | Wang et al. | 427/2 |
| 5,132,095 | 7/1992 | Koshiishi et al. | 422/82.07 |
| 5,169,599 | 12/1992 | Joseph et al. | 422/57 |
| 5,196,350 | 3/1993 | Backman et al. | 436/501 |
| 5,212,063 | 5/1993 | Ofenloch-Hähnle et al. | 435/7.5 |
| 5,242,828 | 9/1993 | Bergström et al. | 435/291 |
| 5,268,306 | 12/1993 | Berger et al. | 436/527 |
| 5,283,079 | 2/1994 | Wang et al. | 427/2 |
| 5,316,784 | 5/1994 | Maurer et al. | 427/2 |
| 5,328,985 | 7/1994 | Sano et al. | 530/350 |
| 5,378,608 | 1/1995 | Marui et al. | 435/7.5 |
| 5,395,754 | 3/1995 | Lambotte et al. | 435/607.4 |
| 5,418,136 | 5/1995 | Miller et al. | 435/5 |
| 5,436,161 | 7/1995 | Bergström et al. | 435/291 |
| 5,468,606 | 11/1995 | Bogart et al. | 435/5 |
| 5,482,830 | 1/1996 | Bogart et al. | 435/5 |
| 5,492,840 | 2/1996 | Malmqvist et al. | 436/518 |
| 5,494,829 | 2/1996 | Sandstrom et al. | 436/518 |

SENSING SYSTEM FOR SPECIFIC SUBSTANCE AND MOLECULE DETECTION

FIELD OF THE INVENTION

The present invention relates to detection and/or quantitation of an analyte of interest or specific substance and, in particular, to a system that includes an instrument for measuring mass associated with a multi-layered sensing unit to determine whether an analyte of interest is present.

BACKGROUND OF THE INVENTION

Sensors and methods for the detection of the presence of substances or molecules in a sample, using a solid-phase assay system, have been described previously. Typically, the sample is put in contact with the sensor, allowing analyte present in the sample to bind to the analyte-specific ligand layer of the sensor. For analysis, the sample may be removed from the sensor. The sensor surface is then analyzed for the presence of the analyte. Sensors can be defined as including immunosensors, affinity sensors and ligand binding sensors, each of which is characterized as involving specific mass change activity in connection with determining whether or not certain molecules or substances are present. Sensors are typically efficient at binding the substance of interest (analyte) and highly sensitive and specific to the analyte. The sensor may consist of one or several layers of various chemical and physical compositions. The composition depends on the nature of the analyte and the matrix in which the analyte is contained. These layers may include any combination of: a solid supporting substrate; attachment layer or layers to bind the substrate and/or subsequent layers in the sensor; any number of intermediate layers; a ligand layer that binds specifically to the analyte. Detection of the analyte bound to the sensor can be achieved by several means including, but not limited to, electrochemical, chemical, and optical methods. Detection of the analyte may be enhanced by various means including enzyme amplification, and the use of a mass-enhanced analyte-specific secondary ligand.

A solid substrate, or base, of the sensor has inherent physical, chemical, electrical, or optical properties that are suited specifically to the detection method employed in the assay. A ligand layer is typically provided above the substrate and an analyte to be detected or measured is bound to the ligand layer. The solid support may be used for the direct binding of the analyte to its surface and subsequent detection. However, depending on the composition, complexity, and/or stability of the analyte or the sample in which the analyte is contained, and the nature of the interactions of the sample/analyte with the solid substrate, it may be necessary to add one or several intermediate layers to the solid support.

Attachment layers may be used as intermediate layers between the solid substrate and the ligand layer if, for example, the ligand layer does not adhere to the substrate, or is destroyed, denatured, destabilized or otherwise inactivated upon binding to the substrate. The surface of the intermediate layer in contact with the solid substrate must adhere tightly to the substrate throughout the preparation and use of the test piece. The surface of the intermediate layer opposite the solid substrate must either be suitable for strong binding of either the ligand layer or another intermediate layer. In this manner, and using these considerations for the nature of the intermediate layers, multiple layers may be assembled, the topmost of which is suitable for the binding of the ligand layer.

The ligand layer forms a sensing surface that is receptive specifically to the analyte of interest when the analyte is present in a sample to be tested. The analyte is thus immobilized onto the sensing surface of the sensor and can be detected by any of the methods mentioned above.

Although some multi-layered sensors such as those outlined above have been described previously in the prior art, development of such sensors, in accordance with the present invention, seeks to improve and enhance their sensitivity. The goal of one element of the present invention, in order to improve this sensitivity, is to immobilize a ligand layer that retains maximum binding capacity for a specific analyte. This usually involves the use of an intermediate attachment layer or layers as described above. This multi-layer molecular film is designed specifically to accommodate downward interaction with the substrate, and upward, optimized interaction with the ligand layer.

Detachment, or delamination, of these intermediate layers from the supporting substrate is a serious problem that must be solved to successfully build a multi-layer sensing surface. Delamination occurs between the substrate and an intermediate layer if the composition of these two components is not conducive to a strong physical or chemical interaction between the components. The interaction between the substrate and intermediate layer may be weakened during the manufacture, assembly, transport, preparation or use of the sensor.

Once an attachment layer or layers is produced that is stable to delamination from the solid support, the topmost of the intermediate layers is used to immobilize a ligand layer specific to the analyte of interest. It is critical that the topmost attachment layer optimizes its interaction with the ligand layer in order to provide maximum binding capacity for the analyte of interest and prevent denaturation, deactivation, or inactivation of the ligand layer. These provisions for the immobilization of the ligand layer are essential to the enhanced sensitivity of the test.

Known sensing systems, in addition to multi-layered sensors for immobilizing analyte that may be present in a test sample, include instrumentation for detecting the immobilized analyte. One class of instrumentation, including surface acoustic wave spectroscopy, ellipsometry, and quartz microbalances, measures the change in mass of the sensor upon immobilization of an analyte. Generally speaking, when the analyte is present in the test sample, it can be detected based on a change in mass at the surface as compared to the mass when no analyte is present in the sample.

Optical instruments in this class, as described in the prior art, direct a beam of light through a number of instrument components or elements to the sensing surface that has been previously exposed to the sample being tested. Light is reflected from the sensor, and its reflected properties, including intensity and various optical properties may be measured. Any change in mass of the sensor due to analyte binding is represented by a change in the properties of the reflected light. In particular, measuring changes in polarization state of the reflected light has proven to be a highly sensitive measurement of mass change. Briefly, the sensor may be analyzed by an appropriate instrument that detects and/or measures the presence of the analyte using light reflected from the analyte or light that is transmitted through the analyte.

The main problem associated with instruments that employ these optical techniques for detection of surface bound analyte involves the accuracy of detection. Since extremely small changes in mass may be indicative of the presence of the analyte, it is a goal of the present invention that the instrument be highly sensitive to enable it to detect such mass changes. Additionally, because these instruments are expected to be utilized in a variety of environments outside of well-controlled laboratory settings, it is a further goal that the instrument design take into consideration a number of factors such as component size, durability and automation of instrument operation.

Based on the foregoing factors and considerations, it would be advantageous to devise a sensor system that overcomes such drawbacks or deficiencies of the prior art by providing a system that includes an instrument that readily functions and cooperates with a sensing unit for detection and/or measurement of specific mass change activity due to the presence of an analyte of interest. The instrument of such a system would be highly sensitive and accurate in connection with the detection and/or measurement related to mass change, while the sensing unit of such a system would immobilize a ligand layer that retains, for all necessary purposes, the analyte of interest.

SUMMARY OF THE INVENTION

In accordance with the present invention, a sensing system is provided that includes a sensing unit and associated processes for making, assembling, and using such a sensing unit. The sensing system also includes a test piece on which is positioned one or more sensing units capable of capturing and immobilizing an analyte or analytes of interest from a test sample, and an instrument for detecting the analyte(s) immobilized on the sensing unit. The test sample containing the analyte of interest may take the form of a true vapor, a liquid or an extracted solid.

In one embodiment, the sensing unit includes a solid reflecting substrate, an analyte-specific ligand layer and a tripartite attachment layer used to immobilize the ligand layer. The solid substrate is preferably any reflective substance other than a free electron metal that provides a base of the sensing unit. The upper surface of the solid substrate would, if improperly isolated from the ligand layer, cause denaturation, decay, or inactivation of the ligand layer. The tripartite attachment layer is defined by a lower binding surface, an insulating intermediate layer, and an upper binding surface.

The tripartite attachment layer used to immobilize the ligand layer may consist of three distinct materials, or different material compositions of a single material, providing that each element of this layer (the lower binding surface, the upper binding surface, and the insulating layer) has properties that are suited particularly for its role in the tripartite attachment layer.

The lower binding surface contacts the surface of the solid substrate and is comprised of a material that adheres tightly to the solid substrate. This lower binding surface provides a durable and stable lamination of the entire attachment layer to the silicon surface. The upper binding surface of the tripartite attachment layer has chemical or physical properties that allow it to immobilize an analyte-specific ligand layer. The insulating layer is located between the lower and upper binding surfaces. significantly, the insulating layer acts to prevent the transfer of various effects from the lower binding surface to the upper binding surface and, additionally, from the upper binding surface to the lower binding surface. The insulating intermediate layer protects the ligand layer from the various effects of the solid substrate. The analyte-specific ligand layer is in contact with the upper binding surface of the tripartite attachment layer. This ligand layer captures and immobilizes a specific analyte when it is present in a sample to be tested. The sensing unit preferably has a number of associated attributes including that each of the material compositions of the lower binding surface and the upper binding surface has properties that are preserved with the use of an effective insulating layer. The tripartite attachment layer may consist of three distinct materials, or different material compositions of a single material, providing that each element of this layer (the lower binding surface, the upper binding surface, and the insulating layer) has properties that are suited particularly for its role in the tripartite attachment layer.

In a related variation, the upper surface of the tripartite attachment layer may be used to bind to a ligand layer that is receptive to or captures a non-specific analyte. That is, the tripartite attachment layer is not limited to use with an analyte-specific ligand layer.

In another embodiment, the sensing unit includes the solid substrate of the first embodiment, such as a reflective substrate other than a free electron metal (e.g. crystalline silicon), two elements or layers of an attachment layer, and an analyte-specific ligand layer. The attachment layer element closest to the silicon surface is comprised of, for example, an organofunctional silial compound. The silane portion of the attachment layer forms a covalent linkage to the silicon substrate surface, leaving the reactive organofunctional group available for further interaction with a second element of the attachment layer. The second element of the attachment layer is usually an organic polymer film that is applied, preferably spin coated, to the organofunctional silial compound layer. This organic polymer film provides a controlled environment to immobilize the analyte-specific ligand layer or to attach the non-specific sample to serve as an attachment platform for the non-specific binding of analyte in the sample.

A sensing surface may include the solid silicon substrate of the first embodiment, a single attachment layer applied using conditions that prevent the attachment layer from delaminating from the solid substrate, and an analyte-specific ligand layer. The attachment layer is, for example, an organic polymer. This single attachment layer provides all three functions described in the first embodiment: binding to the silicon support, immobilizing the ligand layer, and isolating the ligand layer from properties of the solid substrate that may inactivate the analyte-specific ligand layer. The ligand layer captures and immobilizes a specific analyte when it is present in a test sample.

Like the tripartite attachment layer, both the dual element attachment layer and the single attachment layer may be used to bind to a ligand layer that is receptive to a non-specific analyte.

Detection of the analyte may be improved further through various means of mass enhancement. These mass enhancement techniques typically involve the secondary binding of an analyte-specific ligand that may or may not be different from the ligand used to immobilize the analyte on the surface. This secondary binding ligand may be further linked to an additional amplification system. These additional amplification systems include, but are not limited to, enzymes (such as horse radish peroxidase or alkaline phosphatase), macromolecules (such as DNA, RNA or ferritin) or small particulates (such as polystyrene microspheres, metal sols, silica, self-assembling monolayers or film-forming compounds).

Each sensing unit is adapted to be held at a defined location on a test piece or slide. Typically, each test piece is able to support a predetermined number of sensing units.

The defined positions on the test piece include marks, bar codes, or other indicia that are useful in identifying the particular sensing unit on a test piece. The test piece is of a size and shape to be used with and received by an instrument for detecting and/or measuring, when present, an analyte or substance of interest that is bound to one or more of the sensing units on the test piece. The instrument includes a compact housing that includes a number of assemblies or elements. A test piece movement assembly may provide automatic control of the positioning of the test piece, particularly relative to a light beam assembly that is used in detecting whether or not an analyte of interest is present on the current sensing unit being tested.

The instrument may also include a reader assembly for reading the marks or codes on the test piece and regulating the movement of the test piece using the application of power to a motor in order to properly position the test piece and, concomitantly, the sensing unit under test, relative to the light beam assembly.

The housing includes an aperture for receiving the test piece. The housing may further include a user input assembly, such as a keypad, for requesting information and data related to the detection process. The instrument also has a display unit, for example LCD, that displays requested output information, such as the results of the detection process, as well as graphs or plots. The display unit is also useful in communicating available options to the technician or user related to information and data that is available from the instrument. Preferably also, the instrument is able to communicate with an external processing source or computer system that enables the instrument to download data or other information related to the functions that it performs in connection with the detection and/or measurement process.

The light beam assembly includes a source of light that is controlled and directed for obtaining information useful in analyzing the mass of the sensing unit in connection with determining whether or not the analyte of interest is present. In one embodiment, the light beam assembly includes components for providing a number of bounces or reflections of the altered light through the same sensing unit in order to amplify the changes in the reflected light to improve sensitivity. Such sensitivity is particularly advantageous when the substance of interest is present and the mass change of the sensing unit is relatively small and difficult to detect.

With respect to further aspects related to the method or operation for determining whether or not an analyte of interest is present, the test piece having a number of sensing units is inserted into the instrument housing. The test piece movement assembly is controlled by a digital controller having a processor so that it is moved inwardly within the housing until the reader assembly reads a mark or code that is interpreted by the processor,and thus, controls the powering off of the motor of the test piece movement assembly. The light beam assembly provides a beam of light that is controlled and caused to reflect from the sensing unit being tested. Reflected light from this particular sensing unit is collected and analyzed. In certain embodiments for obtaining light from a sensing unit, the instrument is also configurable to provide virtually only s-polarized light or, alternatively, p-polarized light. In such cases changes in the detected signal due to change in polarization state from a particular sensing unit will be a function of any increase or decrease in the mass of the sensing unit. Preferably, such light is linearly polarized; however, circular or elliptical states of polarization can also be utilized. The results of the analysis are stored and available for presentation and/or for the user to obtain and make decisions based on such results.

The stored information includes not only information related to the result of whether or not the analyte of interest is present, but also information related to the identification of the individual test pieces and sensing units.

In one embodiment of the invention, the system further includes a device that has a number of assemblies for providing desired functions associated with test pieces or test performance. A heating assembly includes a number of plates that are heated to enable heat to be conducted to the test piece. The heating assembly also includes a support frame that permits it and the heated plates to be pivoted for access to a number of absorbative members of a humidifying assembly. Each of the absorbative members is soaked with water to enable moisture or vapor to be developed due to the heat generated by the heating assembly. A mixing assembly is also part of the device for mixing the materials associated with the sensing units. A barrier manifold having a number of barrier members is pivotally movable relative to the test piece when it is positioned within the incubation device. The barrier members are useful in avoiding cross-contamination among the number of sensing units with the test piece.

Based on the foregoing summary, a number of key features of the present invention are easily recognized. A system is provided that includes a sensing or assay unit comprising an attachment layer that both substantially reduces the possibility of delamination of the attachment layer from a substrate and immobilizes a ligand layer that is receptive to an analyte of interest when it is present with the sensing unit being tested. In one embodiment, the attachment layer is definable as three layers that include an insulating layer for preserving the integrity and proper functioning of the layers or surfaces that the insulating layer contacts.

The system also may include methods and materials for enhancing the detection and/or measurement of mass change activity of the substance of interest, when present. Such mass enhancement techniques are associated with the sensing unit and assist an appropriate instrument in its detecting or measuring operations by effectively enhancing the presence of the property (mass) being measured.

The system further includes an instrument for receiving a test piece having a number of sensing units in order to determine whether or not one or more of them contains an analyte of interest. The instrument is compact, easy to use in connection with obtaining desired data or other information and has numerous automatic operational features. In particular, the instrument is able to control the position of the test piece to properly align it with a beam of light to be used for detection purposes, conduct the necessary test including analysis of the particular sensing unit and store the results of the test including an identification of the particular sensing unit and the time of the testing. In one embodiment, light is caused to reflect a number of times on the same sensing unit to increase the sensitivity of the instrument. In other variations, only s-polarized light or p-polarized light is obtained to enhance the sensitivity of the detected signal from a sensing unit. The instrument is also able to store and download data to an external computer terminal for additional evaluation or use of the obtained data. Preferably, the system also includes a device for housing the test piece which is beneficial in controlling temperature, humidity and mixing the materials provided with or as part of the sensing unit. This device includes a barrier manifold that acts to prevent each of the tests samples from contaminating each of the other samples.

Lastly, an overall sensing system is provided that has all of the necessary sub-system components for detecting and/ or measuring a substance of interest by relying on mass change activity. These sub-system components readily cooperate and function together in meeting such main objectives. Each sensing unit is properly formed and prepared for testing, including use of suitable mass enhancement techniques that effectively amplify the signal that is detected when the analyte is present. The sensing units on the test piece are properly prepared and accurately positioned relative to the instrument for conducting the desired test. The instrument itself is highly sensitive to mass activity change in connection with determining whether or not the analyte of interest is present.

Additional advantages of the present invention will become readily apparent from the following discussion, particularly when taken into account with the accompanying drawings.

DETAILED DESCRIPTION

Figure 1:
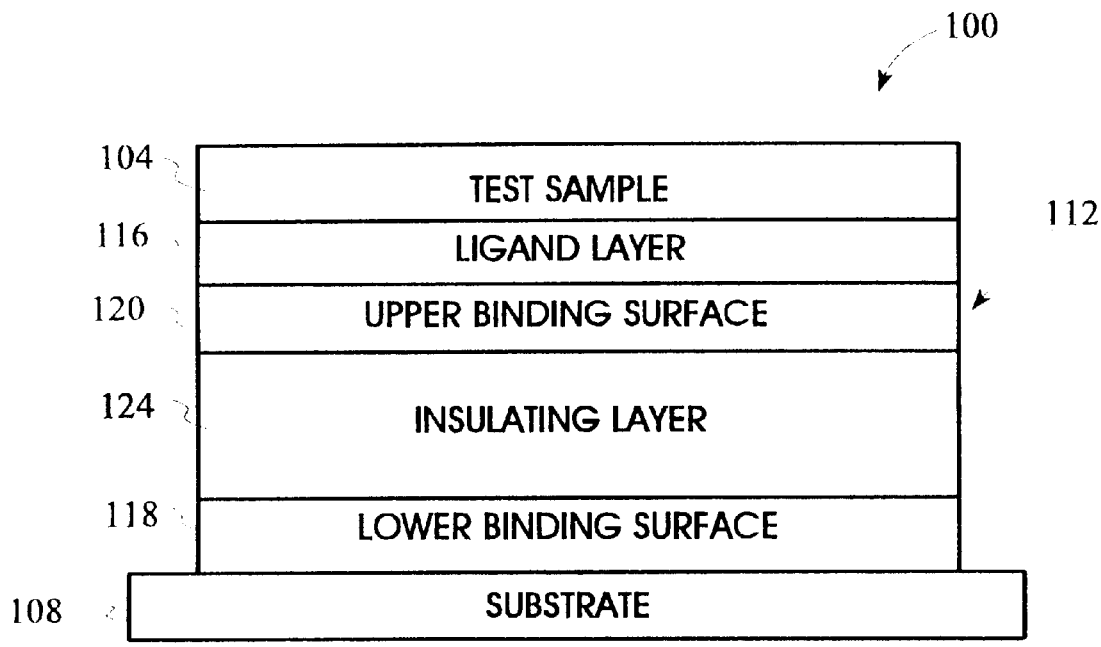
FIG. 1 is a diagrammatic representation of a sensing unit that includes a tripartite attachment layer.

With reference to FIG. 1, an embodiment of a sensing or assay unit 100 of the system of the present invention is schematically illustrated. As seen, the sensing unit 100 includes a number of layers made of different materials. The multi-layered unit 100 provides a number of functions as will be described later herein. A sample 104 is deposited on the unit 100. The sample 104 is to be subsequently tested to determine whether or not it contains a specific analyte or substance of interest. The specific analyte to be tested to determine whether it is present can include any one of a number of different substances, materials and/or macromolecules, such as biological materials, chemicals, peptides and toxins. In one area of applications, the sensing unit 100 is used as part of a testing system and procedure to test for the presence of unwanted or harmful substances in animal or human body fluids. Depending on the results of such testing, appropriate action or steps can be taken.

The layers of the sensing unit 100 include a substrate or base layer 108 that is used as a support member and is made of a material that is useful or compatible with the testing instrument and protocol. In a preferred embodiment, the substrate 108 is other than a free electron metal (if a substrate has characteristics of a free electron metal, it is not acceptable and cannot be used), but is preferably made of a crystalline silicon material that has desired properties for use with a testing instrument that utilizes reflected light in determining whether the analyte of interest is present.

TRIPARTITE ATTACHMENT LAYER

The substrate 108 has an attachment layer 112 joined thereto that is used to immobilize a ligand layer. The attachment layer 112 includes material compositions for performing two main functions. The attachment layer 112 must securely attach or join to the substrate 108 and it must immobilize, without harm or unwanted alteration, one or more capture layers including the ligand layer 116. The ligand layer 116 comprises a known or specific material or macromolecule that properly bonds with the analyte of interest when it is present in the test sample. The ligand layer 116 may comprise a number of different materials such as monoclonal and polyclonal antibodies, antigens, avidin, biotin, nucleic acids, proteins, peptides, and receptors. In a variation of this embodiment, instead of using ligand layer 116, or any other capture layer, there is a direct binding of the analyte, when present, to the tripartite attachment layer 112.

In one embodiment, the attachment layer 112 is tripartite, non-homogeneous and non-porous. Such an attachment layer 112 includes a lower binding surface 118, an upper binding surface 120 and an insulating or intermediate layer 124 disposed between the surfaces 118, 120. Unlike known prior art, the tripartite attachment layer 112 includes three layers having differing material properties for performing a number of functions associated with establishing desired bonding and insulating functions. The lower binding surface 118 is characterized by a material composition that causes it to be adequately bonded to the substrate 108. Such a bonding adequately resists detachment or delamination of the lower binding surface 118 from the substrate 108. The lower binding surface 118 actively adheres or displays enhanced binding attributes to the substrate 108 through one or more binding mechanisms or techniques, such as adsorption, electrostatic, chemical, covalent or ionic means. Preferred techniques or means provide a durable and stable lamination of the attachment layer 112 to the substrate 108. The upper binding surface 120 preferably consists of a material or materials that are different from the material composition of the lower binding surface 118. The upper binding surface 120 requires different attributes or properties since its primary function is to provide a proper binding environment for the ligand layer 116 so that the ligand layer 116 is not subject to deformation, denaturation, stearic alteration, or partial or total inactivation of the ligand(s) that make up the ligand layer 116. Typically, such macromolecules require a controlled immobilization environment to retain such functional attributes. A failure to retain such attributes results in an inability of the ligand layer 116 to bind to a viable analyte of interest when it is present.

The insulating layer 124 is a protective or barrier layer between the lower and upper binding surfaces 118, 120. This layer 124 has two key functions. The insulating layer 124 prevents unwanted effects or activities to be transmitted in each of two directions. In a first direction, unwanted or potentially harmful effects on the upper binding surface 120 due to the material composition of the lower binding surface 118 or the substrate 108 are controlled or prevented by the insulating layer 124. In a second direction, such effects on the lower binding surface 118 or the substrate 108 due to the material composition of the upper binding surface 120 are prevented from occurring. The unwanted effects involve the transfer of potentially harmful electrostatic, ionic, hydrophobic or covalent properties to one of the two surfaces 118, 120 from the other of the two surfaces. The insulating layer 124 also prevents the transfer of unwanted effects that may be attributable to the capture layer including ligand layer 116 or any other layer, material or sample that may be included with the sensing unit 100.

Each of the lower and upper binding surfaces 118, 120 has a material or materials composition that is different from the material or materials composition of the insulating layer 124. Each of these two binding surfaces 118, 120, requires properties in order to properly function that are different from the insulating or protective layer. The insulating layer 124 may be homogeneous or may be non-homogeneous, such as including a gradient of different materials. Although the tripartite attachment layer 112 may be non-porous, or effectively non-porous, and resists permitting liquid to flow through it, the insulating layer 124 is the region or section of the tripartite attachment layer 112 that inhibits such passage of liquid. The lower and upper binding surfaces 118, 120 need not be impervious or non-porous. Related properties of the insulating layer 124 include its ability to resist or oppose delamination forces or activities for relatively long periods of time.

The compositions of the lower binding surface 118, the upper binding surface 120 and the insulating layer 124 can include one or more of different materials or groups of materials that are appropriate in performing the functions and including the properties required of such surfaces and layer. In one embodiment, the substrate 108 includes, for example, commercially available crystalline silicon that may or may not have a native oxide layer. The tripartite attachment layer 112 can include any combination of, for example, the following materials: inorganic or organic monomeric and polymeric compounds. Examples of materials that can by utilized for the three sections of the tripartite attachment layer include: 6-azidosulfonylhexyltriethoxy silane, aminoethylamino-propyl trimethoxy silane, aminopropyltriethoxysilane, 3-isocyanatopropyltriethoxysilane, phenyltriethoxy-silane, poly(ethylene)glycol, poly(ethylene)oxide, nitrocellulose, paralene, nylon, polyester, polyimides, polyurethane, polystyrene, avidin (and its derivatives), and biotin, and any combination thereof.

In certain embodiments, the attachment layer 112 has the following: inorganic monovalent (non-polymeric) compounds and/or organic monovalent and/or polyvalent compounds that either do not have particles or do have particles that retain their particle size (do not coalesce) of at least 40 microns and each of these has linear backbone (non-branching, random and/or irregular) structures including, for example, polystyrene, polyurethane, polyethylene glycol, avidin-biotin, and/or combinations thereof.

Figure 2:
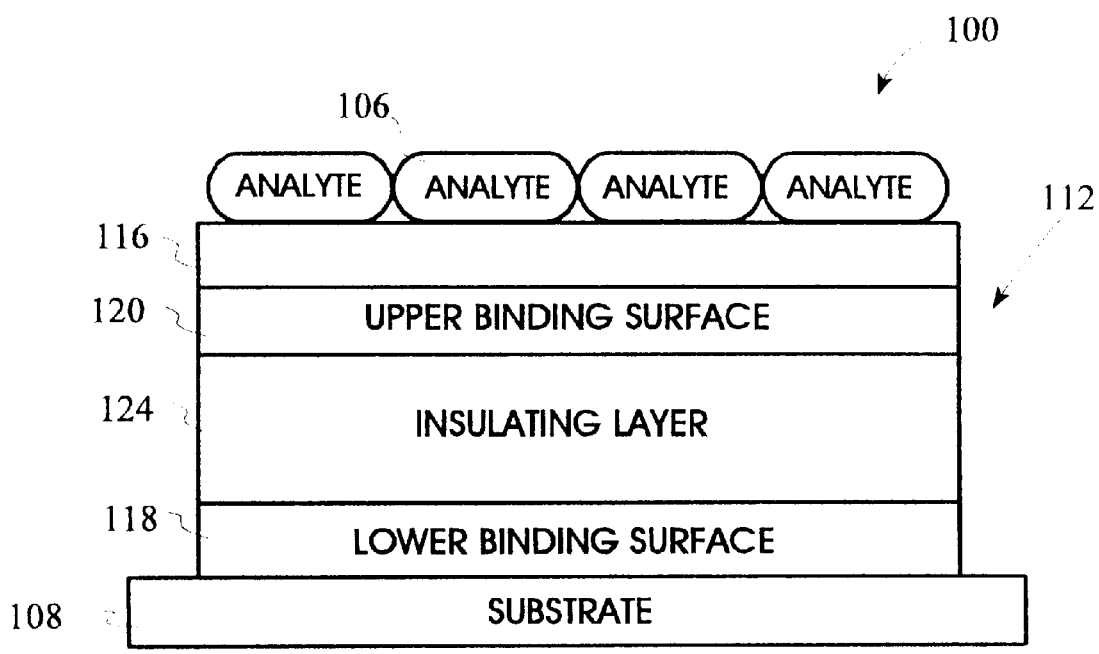
FIG. 2 is a diagrammatic representation of the sensing unit of FIG. 1 illustrating the resultant sensing unit after certain process steps have been conducted and when the analyte of interest is present.
Figure 3:
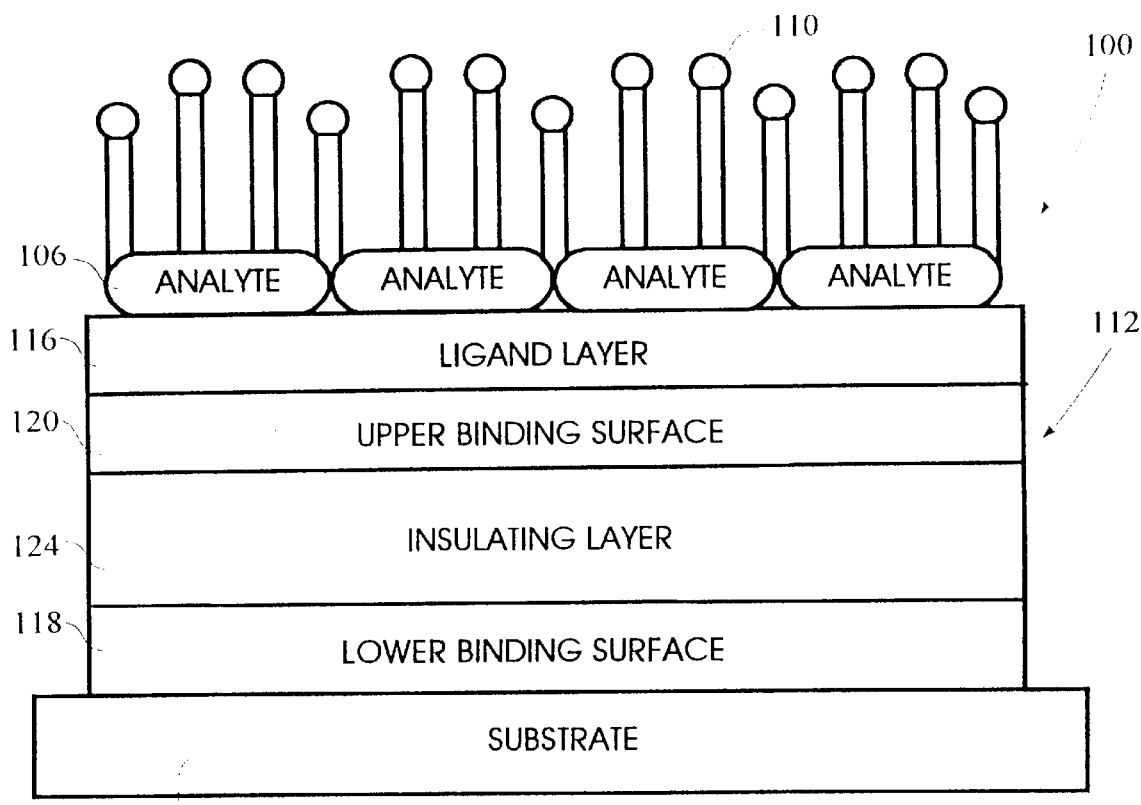
FIG. 3 is a diagrammatic representation of the sensing unit of FIGS. 1 and 2 in which a mass enhancement composition is also utilized.

With reference to FIG. 2, a further depiction of the sensing unit 100 is provided that illustrates the state of the sensing unit 100 after a number of assay process steps have been conducted that will be described in greater detail later herein in the context of a second embodiment of a sensing unit but which steps are also applicable to the embodiment of FIG. 2. Essentially the only substance remaining after such steps is the analyte of interest 106, when present. The analyte of interest 106 is bound or immobilized on the accepting or capturing ligand layer 116. At this stage of its preparation, the sensing unit 100 can be positioned for testing using an appropriate instrument. Alternatively and preferably, as seen in FIG. 3, one or more mass enhancement substances or materials 110 used effectively amplify the mass change, when present, that is being detected or measured. These mass enhancement techniques can take one or more different forms including kinetic-active mass enhancement, passive mass enhancement and a self-assembling amplification system. Mass enhancement substances will be subsequently described in connection with certain examples. These mass enhancement substances improve the detection of the analyte of interest 106 when it is present and usually involve the secondary binding of an analyte-specific ligand, which may be further joined to additional amplification systems.

DUAL ELEMENT ATTACHMENT LAYER

Figure 4:
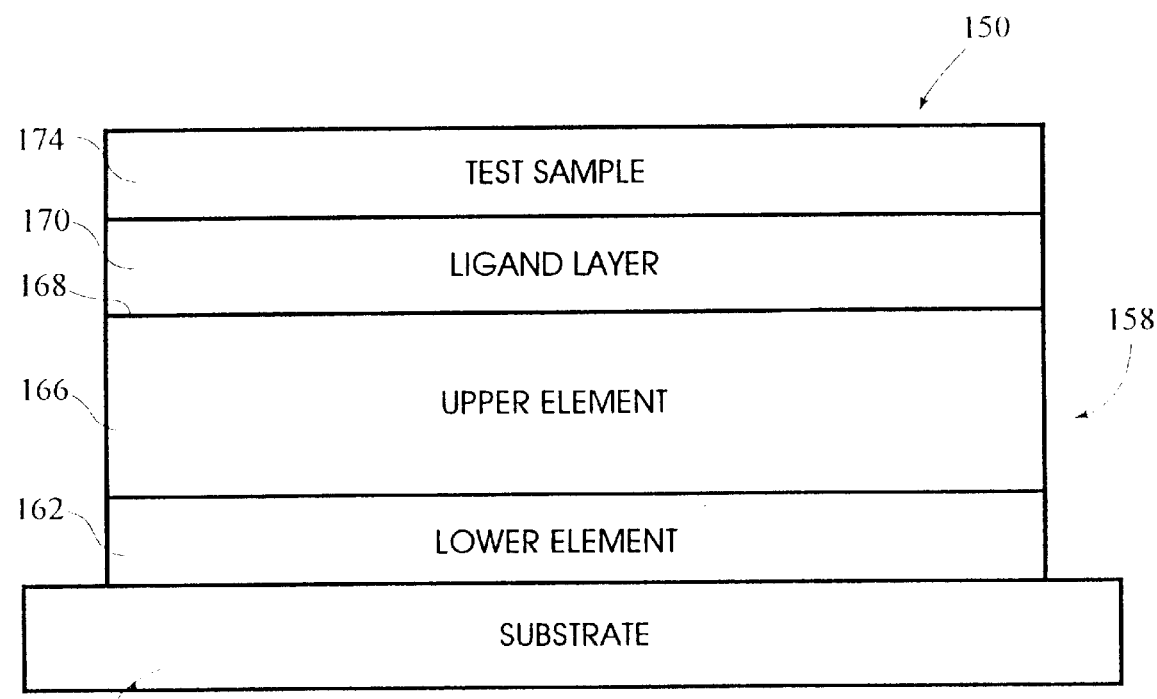
FIG. 4 diagrammatically illustrates a particular sensing unit that has a dual attachment layer.

Another embodiment of a sensing unit is schematically illustrated in FIG. 4. This embodiment includes a dual element or laminate attachment layer, instead of a tripartite attachment layer. This dual element layer, unlike known prior art, is made of different materials including an organofunctional silial compound and an upper element that attracts or bonds to a desired ligand. This sensing unit 150, like the first embodiment, includes a substrate 154 made of a silicon-based material such as a silicon wafer. The attachment layer 158 includes a lower element 162 that has an organofunctional silial compound including, for example, 6-azidosulfonylhexyltriethyoxy silane and aminopropyltriethoxysilane.

The lower element 162 has properties like the lower binding surface 118 of the first embodiment including primarily providing a durable and stable attachment to the substrate 154. The dual attachment layer 158 also includes an upper element 166 that is bound to the lower element 162 by one or more of an adsorption, covalent, ionic, chemical and/or electro-static attachment. Importantly, the upper element 166 must have an outer surface 168 that causes a capture layer including a ligand layer 170 to be bound thereto. In the dual attachment layer embodiment, the outer surface 168 and the remaining portions of the upper element 166 are homogeneous. The capture layer including ligand layer 170 has the same functions and properties and can be comprised of the same material compositions as the capture layer of the first embodiment. A test sample 174 is provided on the ligand layer 170, similar to that in which the test sample 104 is provided on the ligand layer 116 of FIG. 1.

Figure 5:
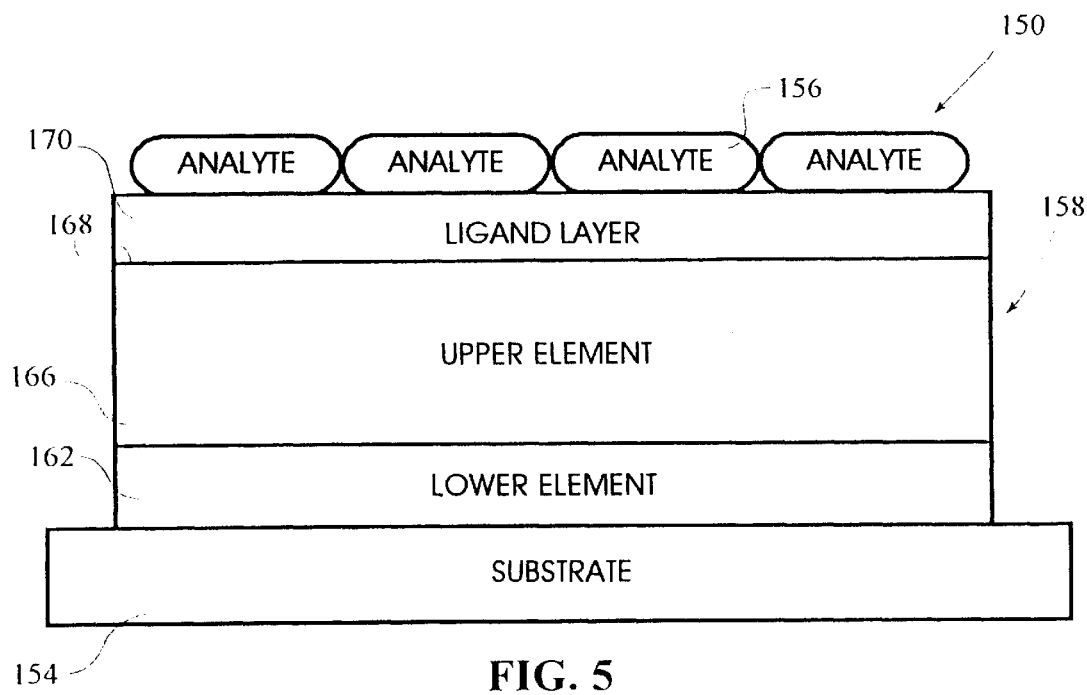
FIG. 5 diagrammatically illustrates the sensing unit of FIG. 4 after certain process steps have been conducted and in which the analyte of interest is present.
Figure 6:
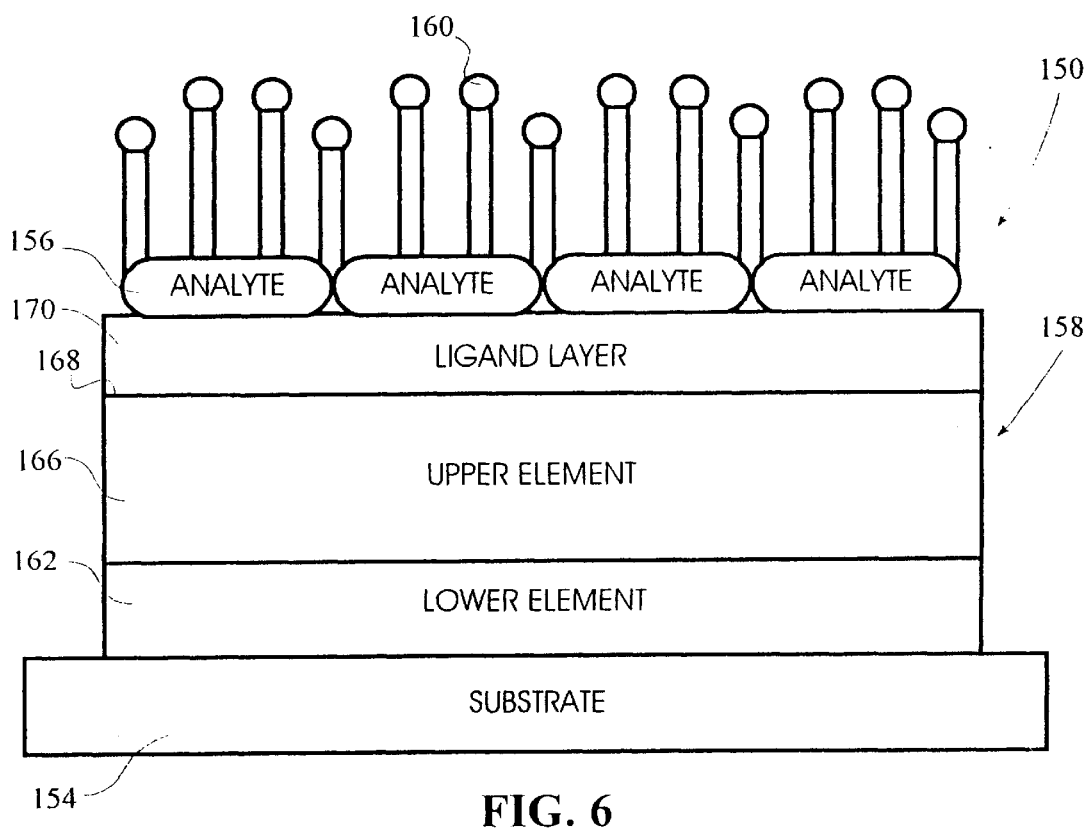
FIG. 6 diagrammatically illustrates the sensing unit of FIGS. 4 and 5 in which a mass enhancement composition is also utilized.

Like the embodiment of FIGS. 1–3, the sensing unit 150 is prepared for testing whether or not an analyte of interest is present. As seen in FIG. 5, after certain process steps that will be subsequently discussed, the analyte of interest 156 is illustrated as being bound to the ligand layer 170. At this stage, the sensing unit 150 may be positioned for testing using, for example, the instrument and variants thereof that will be described later herein. Preferably, mass enhancement systems or substances 160 are provided on the analyte of interest 156. Such a mass enhancement system 160 performs the same functions that are provided in the embodiment of FIGS. 1–3.

Figure 7:
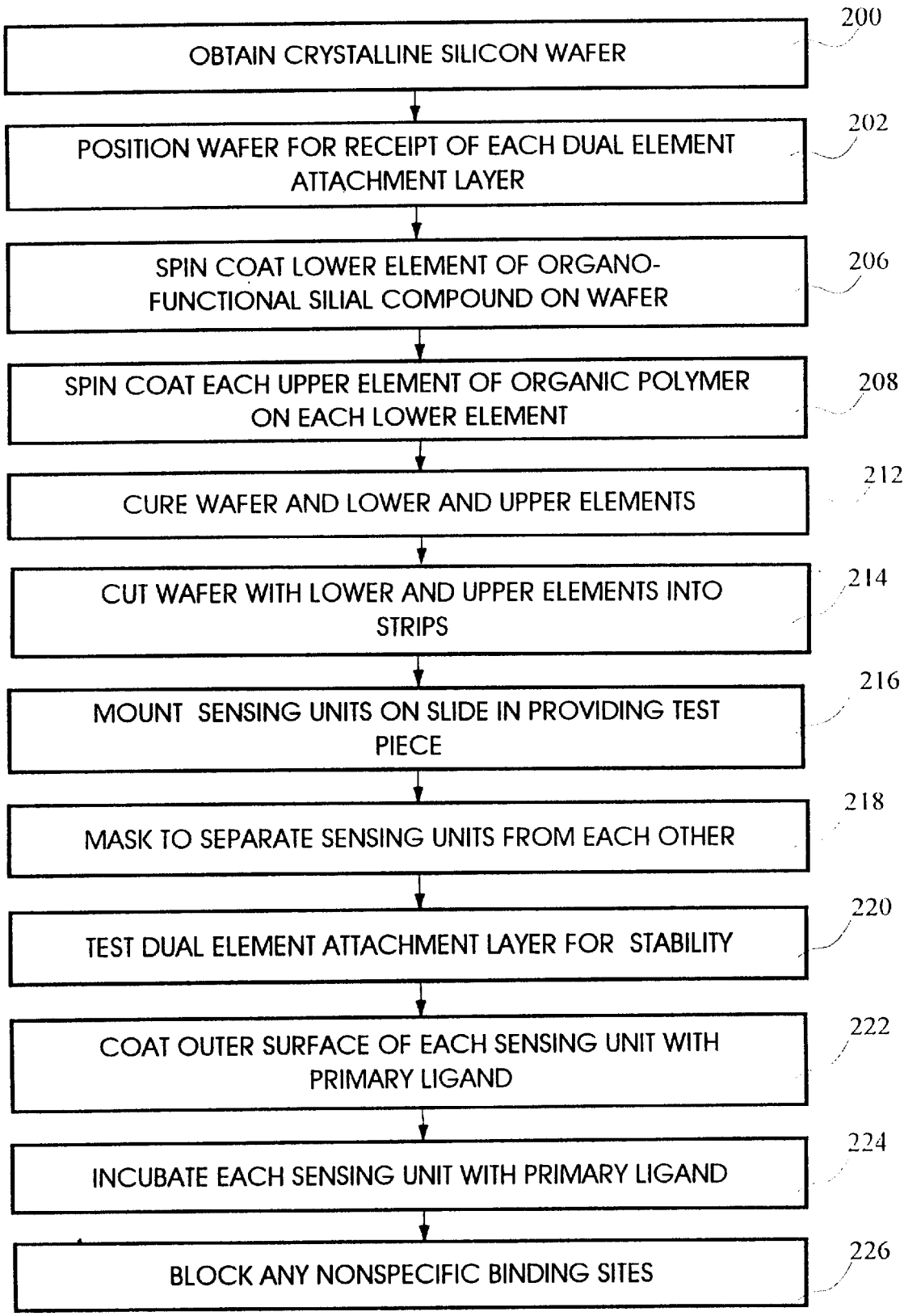
FIGS. 7 and 8 are flow diagrams related to the making and use of the sensing unit of FIGS. 4–6.
Figure 8:
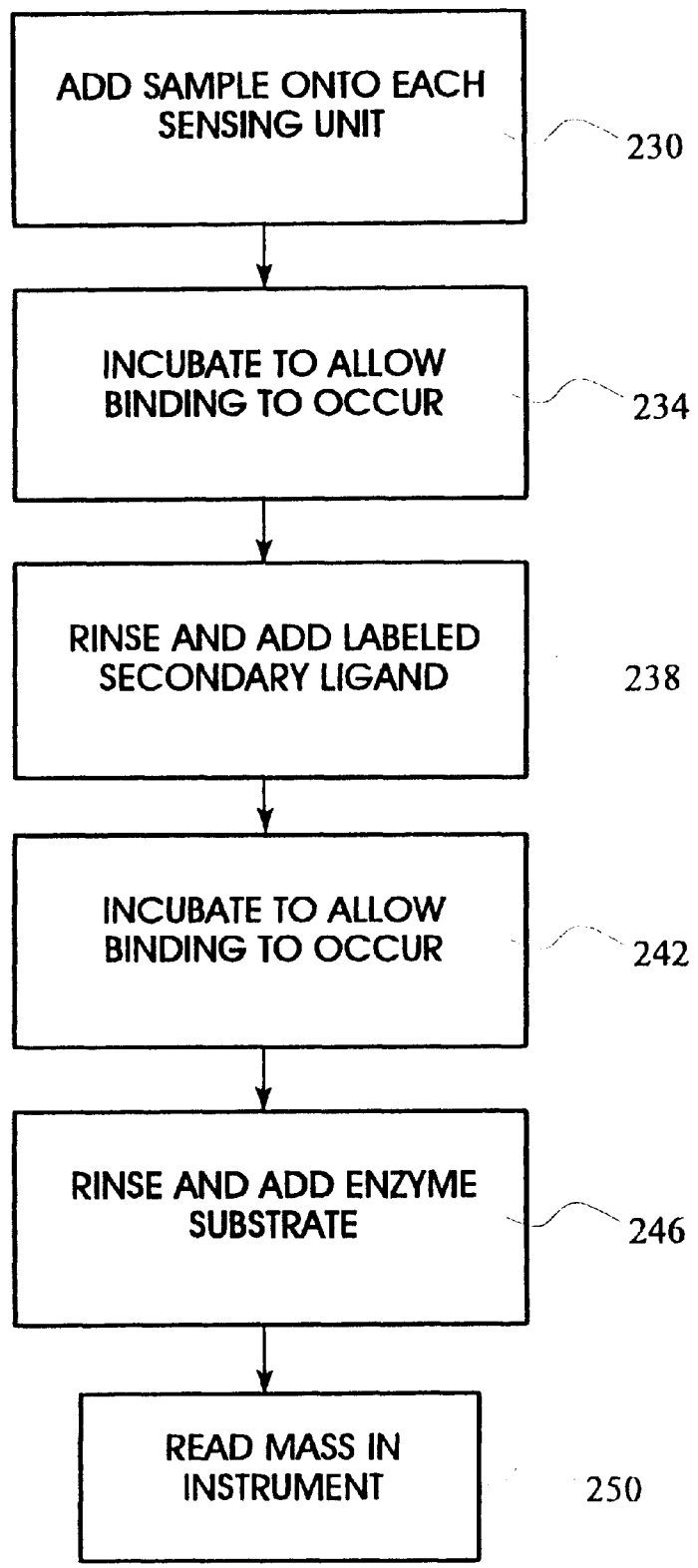

With regard to further details of the composition and method of making the dual element embodiment, reference is made to FIGS. 7 and 8. As provided in the flow diagrams, together with subsequent Examples, 1–3, a number of steps are involved in the making of the sensing unit 150. In particular with reference to FIG. 7, at step 200, a crystalline silicon wafer is obtained. At step 202, the wafer is positioned in a spin-processor for subsequent receipt of the dual element attachment layer. Next, at step 206, an organofunctional silial compound, such as 6-azidosulfonylhexyltriethoxysilane, is spin coated onto the wafer. At step 208, an organic polymer, such as polystyrene, is next spin coated onto each lower element 162 to form each upper element 166. As described at step 212, the wafer and the lower and upper elements 162, 166 are then baked at a sufficient temperature for a suitable time period in order to cure them.

As noted at step 214, the wafer is cut into strips to form each dual element attachment layer 158 that includes the lower and upper elements 162, 166.

In accordance with step 216, a number of sensing units are then mounted on a glass slide. At step 218, a masking step is performed by which each sensing unit is separated from the others in a manner that reduces potential contamination between or among the sensing units, as well as such placement and separation of the sensing units being compatible with the placement and location of identifying bar codes or other indicia.

The dual element attachment layer 158 may be tested for stability at step 220 but need not be. In particular, the attachment layer 158 may be tested to determine its ability to resist or oppose delamination forces or activities.

At step 222, a primary ligand layer 170 is coated to the outer surface of each sensing unit 150. As set out at step 224, the dual element attachment layer 158 and accompanying ligand layer 170 are then baked at a determined temperature for a sufficient time in order to incubate the primary ligand layer 170. Next, at step 226, any additional primary ligand binding sites in each sensing unit are blocked to prevent unwanted, non-specific binding. Such blocking is usually preceded by a rinsing and drying of each sensing unit 150.

With reference to FIG. 8 at step 230, a test sample is then deposited onto each sensing unit 150. The primary ligand layer 170 comprises a known or specific molecule that properly bonds with the analyte of interest when it is present. After adding the test sample, a further incubation is conducted at step 234 in order to allow specific binding of the analyte, when present, to occur.

About the time the testing or assay is to be performed, the blocking composition is rinsed away and, preferably, a secondary ligand is added, in accordance with step 238. At step 242, each sensing unit 150 is once again incubated including, in this embodiment, the primary and secondary ligands and an analyte of interest. As previously noted, it is typically beneficial to include a mass enhancement composition. Hence, at step 246, after the incubation and secondary ligand binding, a further rinsing is conducted and then a mass enhancement composition is added, such as an enzyme substrate. Now each sensing unit 150 is ready to be utilized with a detecting or measuring instrument to read or detect any change in mass in the particular sensing unit 150 due to the analyte of interest, when present, at step 250.

Although the foregoing description relates to the method of making the dual element attachment layer, such steps are equally applicable to a process for making the tripartite attachment layer, except where differences may arise due to the tripartite nature of the tripartite attachment layer, as compared to the dual element attachment layer.

Further detailed explanations of the steps denoted in FIGS. 7 and 8 are provided in the following Examples in which Example 1 relates substantially to the steps of FIG. 7 and Examples 2 and 3 relate to the steps of FIG. 8 and some of the steps of FIG. 7.

EXAMPLE 1

A batch of monocrystalline silicon wafers was obtained having polished silicon wafer surfaces with surface native dioxide thicknesses. The wafers were then positioned in a spin-processor for receipt of the dual element attachment layer.

A 2% 6-azidosulfonylhexyl triethoxysilane (azido-silane) in solution of 95% 200 proof ethanol and 5% $dH_2O$ with 1 drop 1N sodium hydroxide was prepared. The azido-silane solution was spin coated onto the silicon wafer by placing a 300 $\mu$l sample of the azido-silane solution in the center of the silicon wafer while the wafer was spinning at 5,000 rpm in a dry $N_2$ environment. The azido-silane coated wafer was then spun dry, spin rinsed with 1 mL of 200 proof EtOH, and baked at 110° C. for 10 minutes.

A 0.5% 212,000 MW styrene (30–33 mV) in toluene solution was prepared. The styrene solution was spin coated onto the azido-silane layer by placing a 500 $\mu$l sample of the styrene solution in the center of the azido-silane coated wafer while the wafer was spinning at 5,000 rpm in an ambient environment. The dual element attachment layer and wafer were then baked at 1000° C. for 18 to 20 hours and the attachment layer was then checked for attachment stability.

EXAMPLE 2

Rabbit anti-Bacillus globigii polyclonal antibodies are diluted to 9 $\mu$g/mL in 50 mM HEPES buffer (pH 8.0), and 15 μL of this diluted capture antibody are dispensed onto each sensing unit in the test piece. The test piece is then incubated for one hour at 37° C. under high humidity conditions. After rinsing with distilled water and drying the test piece with compressed nitrogen gas, any additional protein binding sites in the sensing units are blocked by adding 18 μL StabilCoat™ to each sensing unit. After incubation for one hour at 37° C., excess liquid is removed by aspiration, and the test piece may be stored at 4° C. until use.

When the assay is to be carried out, the excess blocking protein is rinsed away using distilled water. Fifteen microliters of sample (diluted into Bacillus globigii Sample Buffer consisting of 50 mM HEPES, pH 8.0, with 0.2% bovine serum albumin, 0.01% Tween®-20) are dispensed into the sensing units, and the test piece is incubated at 37° C. for one hour. The sensing units are then rinsed with distilled water and dried with compressed nitrogen gas.

In the next step, 15 μL biotinylated goat anti-Bacillus globigii polyclonal antibodies (diluted to 2 μg/mL in anti-Bacillus globigii Sample Buffer) are dispensed into each sensing unit. The test piece is incubated for thirty minutes at 37° C. The reaction is stopped by rinsing the test piece with distilled water and drying with compressed nitrogen gas. Next, 10 μL streptavidin/polymerized horseradish peroxidase conjugate (Sigma Chemical Company; St. Louis, Mo.), diluted 1:6000 in Bacillus globigii Sample Buffer, are added. The test piece is incubated for thirty minutes at 37° C., and the test piece is then rinsed with distilled water and dried with compressed nitrogen gas.

Finally, 10 μL TMB Reaction Substrate (Kirkegaard Perry Laboratories; Gaithersburg, Md.) are added to each sensing unit. After incubation for 15 minutes at 37° C., the reaction is stopped by rinsing the test piece with distilled water. The test piece is dried with compressed nitrogen gas, and the amount of reaction product is measured on the instrument.

EXAMPLE 3

Sensing units in the test piece are coated with 15 μL of rabbit anti-Listeria polyclonal antibodies, diluted to 23 μg/mL in PBS (10 mM phosphate buffer, pH 7.4, containing 150 mM NaCl). After incubating the test piece for none hour at 37° C. under high humidity conditions, the test piece is rinsed with PBST (PBS containing 0.05% Tween®-20), following by rinsing with distilled water. The test piece is then dried with compressed nitrogen gas. Any additional protein binding sites are blocked by adding 20 μL bovine serum albumin, 30 mg/mL in PBS, to each sensing unit. After incubation for 30 minutes at 37° C., excess liquid is removed by aspiration, and the test piece may be stored at 4° C. until use.

In the next step, 15 μL sample, consisting of heat-killed Listeria in media, is added to the sensing units. The test piece is incubated for 30 minutes at 37° C., and then rinsed with PBST and distilled water. The test piece is dried with compressed nitrogen gas. Next, 15 μL rabbit anti-Listeria polyclonal antibody/horseradish peroxidase conjugate (Kirkegaard Perry Laboratories), diluted 1:500 in Biostride® conjugate diluent, are added to each sensing unit. The test piece is incubated for 30 minutes at 37° C., rinsed with PBST and distilled water, and then dried with compressed nitrogen gas.

Finally, 15 μL TMB Reaction Substrate (Kirkegaard Perry Laboratories) are added to each test well. After incubation for 15 minutes at 25° C., the reaction is stopped by rinsing the test piece with distilled water. The test piece is dried with compressed nitrogen gas, and the amount of reaction product is measured on the instrument.

INSTRUMENT AND SYSTEM OPERATION

Figure 9:
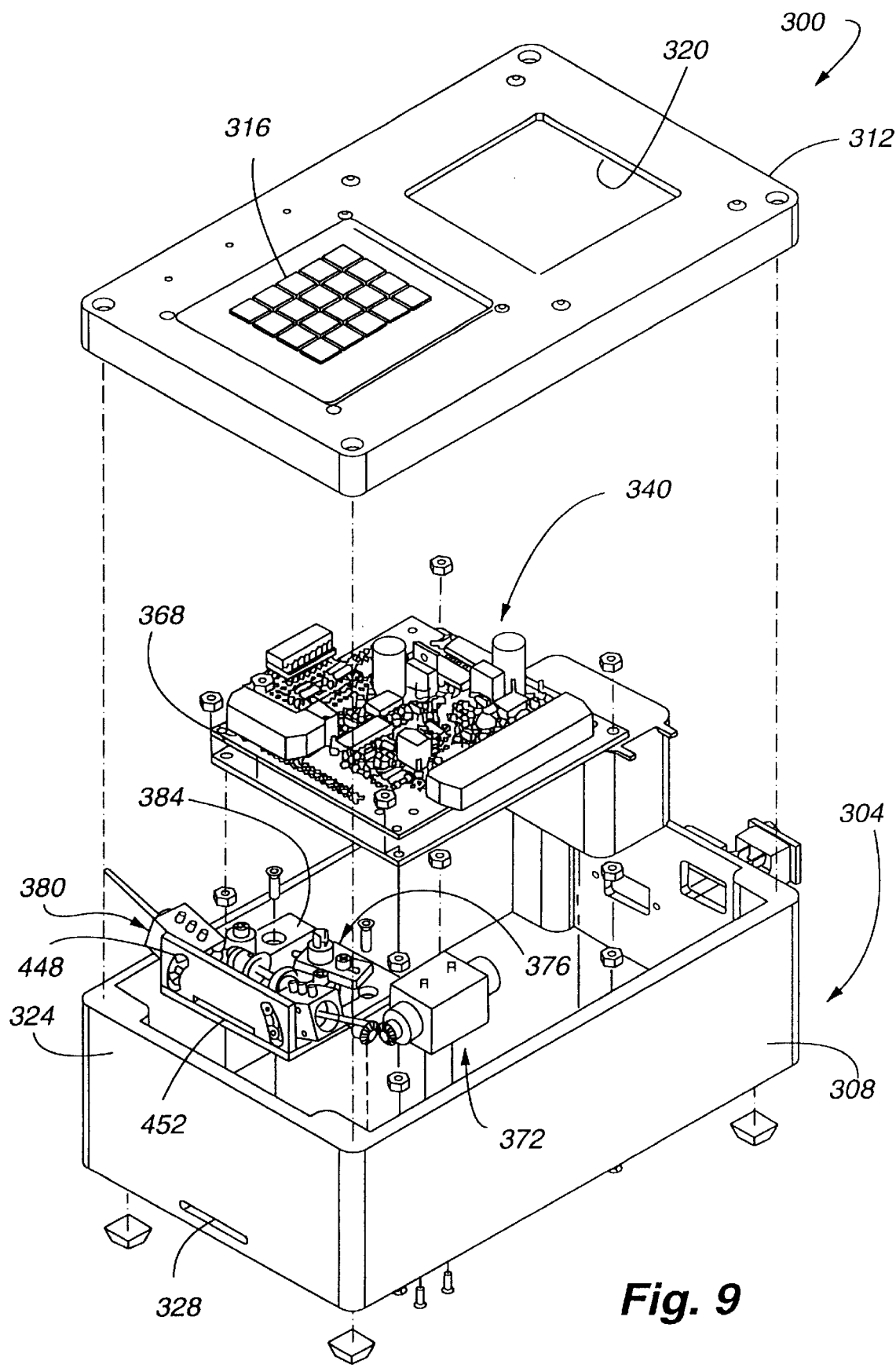
FIG. 9 illustrates an exploded view of an instrument of the present invention involved in the detection and/or measurement process.
Figure 10:
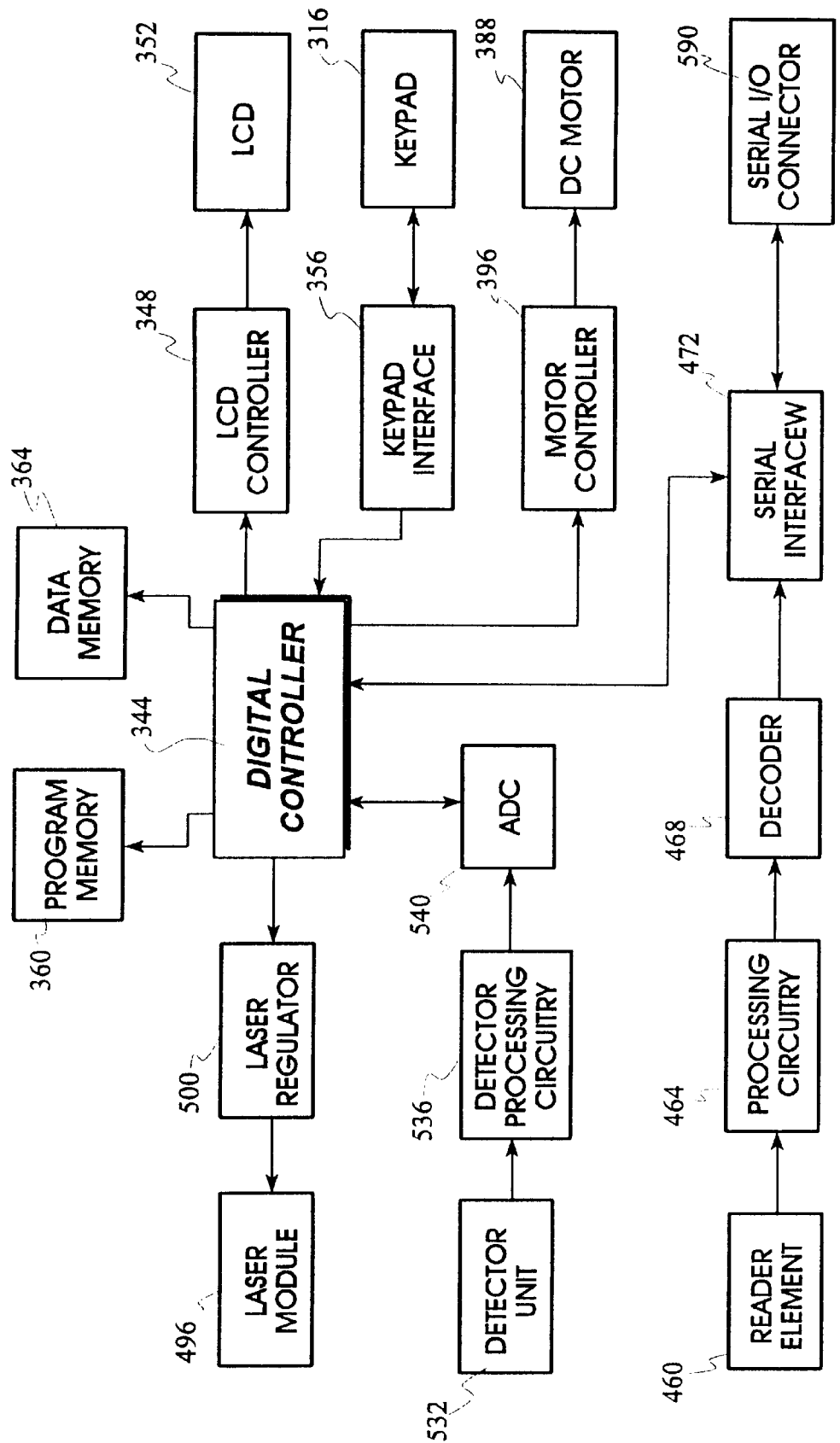
FIG. 10 is a block diagram of major components of the instrument used in analyzing the sensing units and in controlling positioning thereof.
Figure 11:
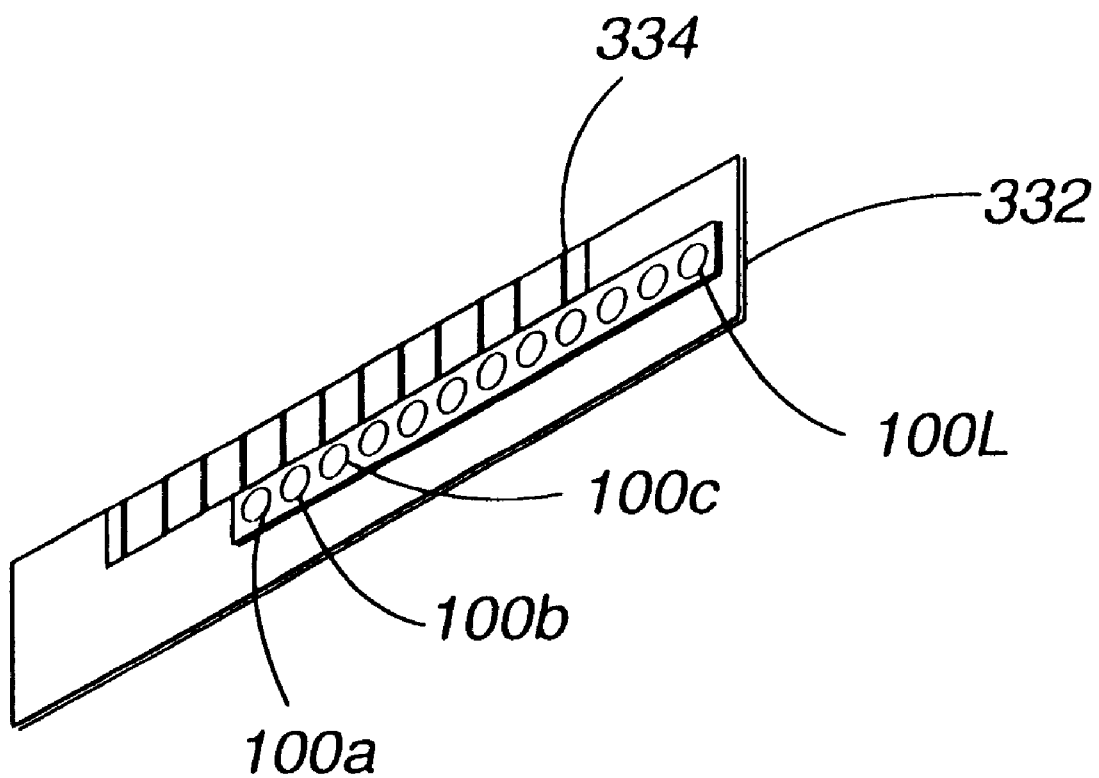
FIG. 11 is a perspective view of a test piece.

With reference to FIGS. 9 and 10, the system for detecting a specific substance or analyte of interest also includes an instrument 300 for obtaining and analyzing data related to the determination of whether or not the analyte of interest is present with a sensing unit 100. The instrument 300 includes a housing 304 for containing assemblies and components utilized in the detection and analysis process. The housing 304 is characterized by its compact size and relatively small footprint. Its compact size is achieved by specific selection and arrangement of such assemblies and components within the housing 304. The housing 304 includes a lower containing unit 308 having a number of walls and an upper cover 312 that is connected to the lower containing unit 308. The cover 312 has an upper face that includes an input unit or keyboard 316 by which the technician or user can input information including requests for data to the instrument 300. The upper face also has a window 320 for receiving a liquid crystal display (LCD) 352 (FIG. 10) that is useful in displaying menus or other information for selection, together with results of the analysis conducted by the instrument 300, such as graphic plots of data related to the detection process. An end wall 324 of the lower housing unit 304 has a receiver slot 328 formed near the bottom of this end wall 324. The receiver slot 328 is configured and of a size to receive a test piece or slide 332. As seen in FIG. 11, the test piece 332 is an elongated, relatively flat member that is able to hold a number of sensing units 100, each of which is spaced from any other such unit 100. The test piece 332 has indicia 334 for indicating the location and/or identity of the particular sensing unit 300. That is, such indicia 334 may include one or more marks associated with or located at each sensing unit 100a–100l. Consequently, when such a mark is read or detected by the instrument 300, this read information can be used to initiate the analysis and detection process. Additionally or alternatively, such indicia 334 may include identification information, such as in the form of a bar code associated with or located adjacent to each sensing unit 100a–100l. The bar code for each sensing unit represents the identity of the particular sensing unit 100a–100l. Accordingly, such bar code information can be used to maintain or record identity information for the particular sensing unit that is being tested and distinguish it from other sensing units.

Returning to FIGS. 9 and 10, one of the assemblies of the instrument 300 is a controller assembly 340. The controller assembly 340 has a number of electronic components, including a digital controller 344 that is responsible for controlling and interacting with a number of devices or elements. The digital controller 344 includes one or more processors that are involved with determining whether or not a specific analyte of interest is present in the sensing unit 100 being tested using data that the processor receives from other components of the controller assembly 340. The digital controller 344 communicates with a LCD controller 348, which is used in controlling and providing the presentation of information by the liquid crystal display (LCD) 352, under the ultimate control of the digital controller 344. Similarly, the digital controller 344 communicates with the keypad 316 through a keypad interface 356 before sending such information to the digital controller 344. The controller assembly 340 also includes memory storage for storing data and executable code. In that regard, a program memory 360 and a data memory 364 communicate with the digital controller 344. The program memory 360 stores programmed code or algorithms for analyzing the data-related signals that are received by the digital controller 344, including those related to detecting the presence of an analyte of interest. The data memory 364 is utilized to store results associated with the detection process, such as values related to the results of the detection process.

Returning to FIG. 9, the components and assemblies of the controller assembly 340 are mounted on one or more printed circuit boards 368 that are sized to be contained within portions of the lower containing unit 304. Also included within the lower containing unit 304 and in communication with the digital controller 344 is a number of data providing/generating or peripheral assemblies, with at least portions thereof disposed below the printed circuit board(s) 368. More specifically, a test piece control assembly 372, a reader assembly 376 and a light beam assembly 380 are provided, with at least some elements of each of these three assemblies being fixed to a mounting plate 384.

Figure 12:
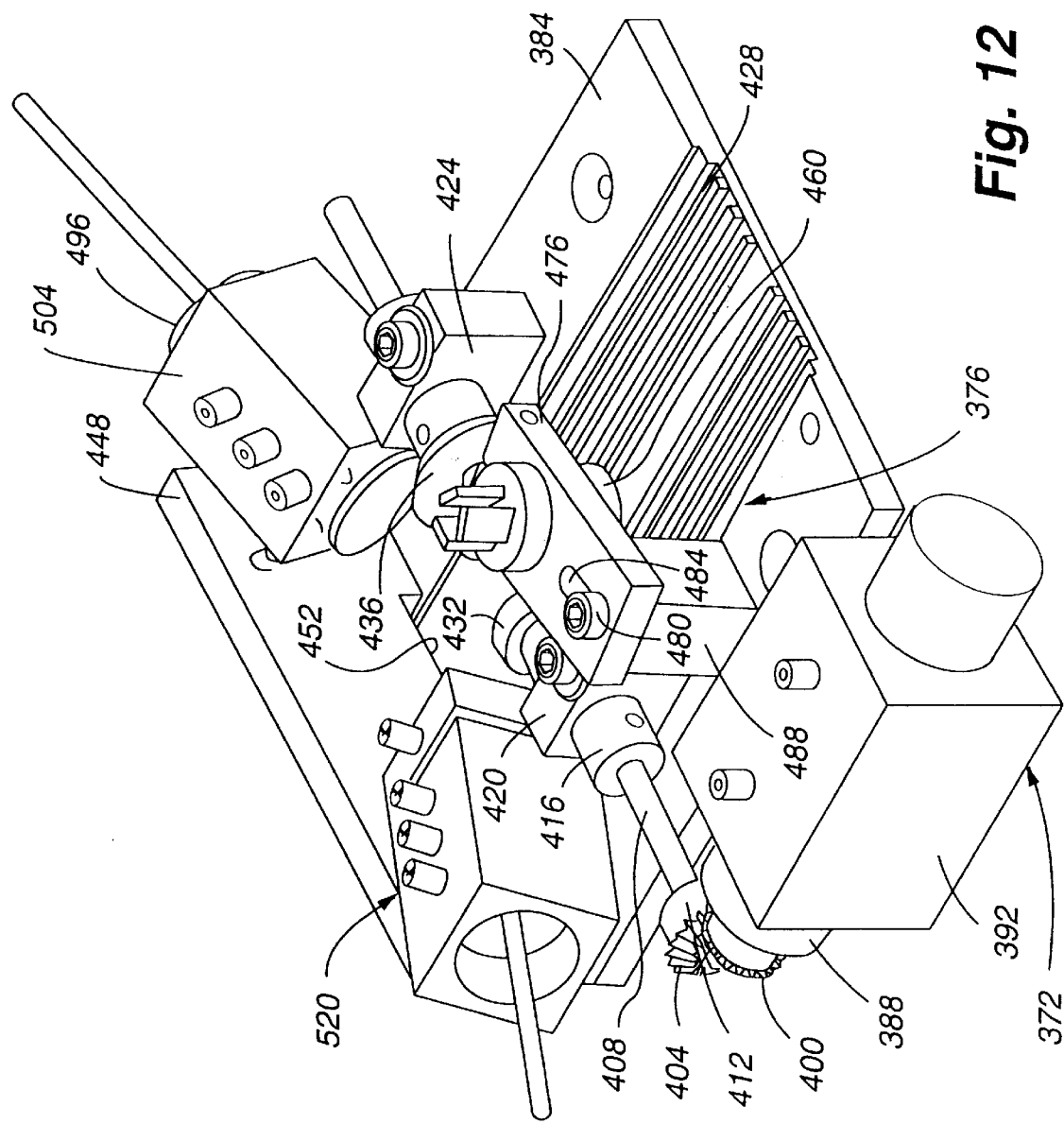
FIG. 12 is an enlarged, diagrammatic view of the light beam assembly, the test piece movement assembly and the reader assembly used in an instrument of the present invention.
Figure 13:
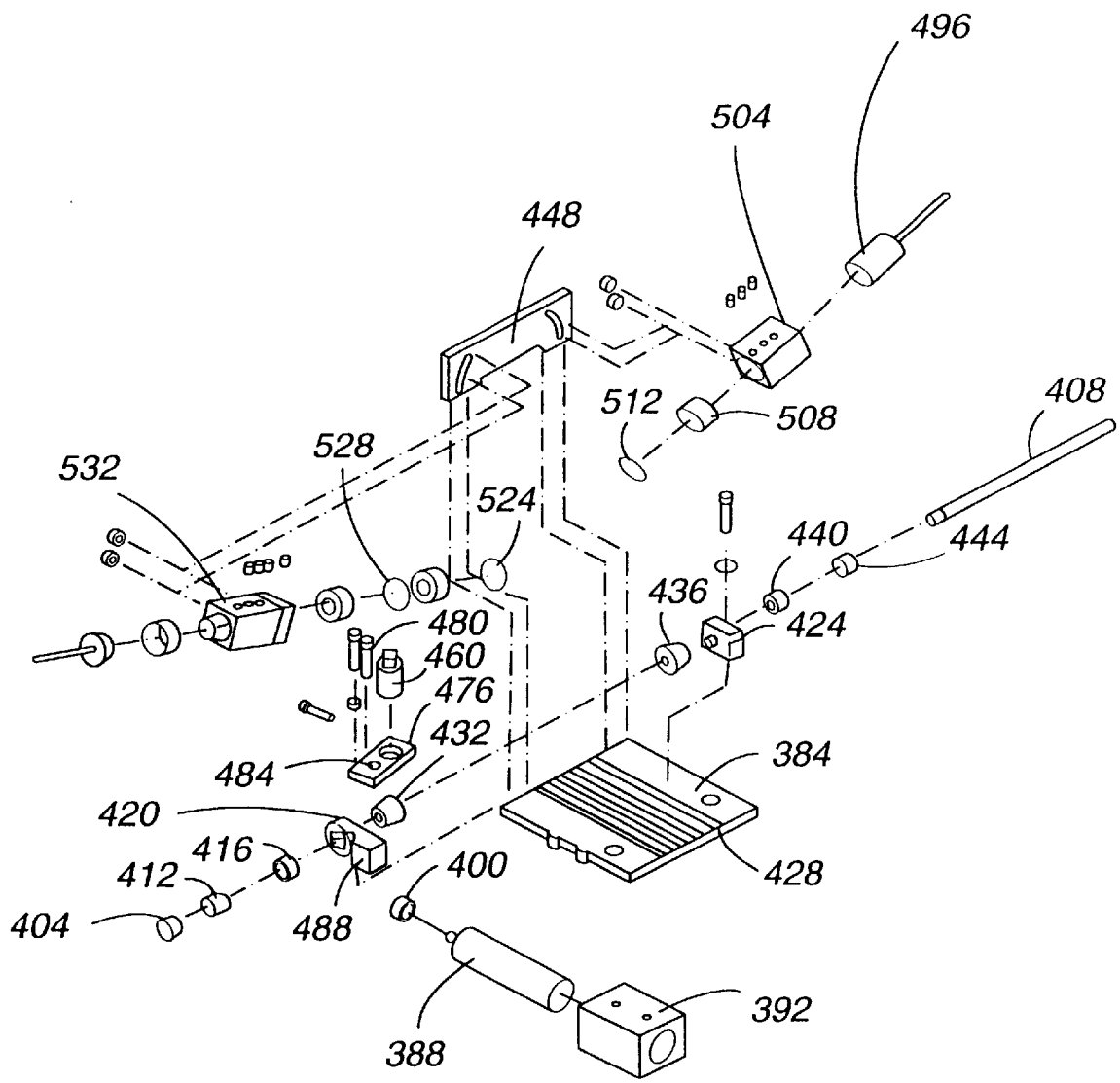
FIG. 13 is an exploded view illustrating a number of components of the light beam assembly, the test piece movement assembly and the reader assembly of the embodiment of FIG. 12.

With reference to FIGS. 12 and 13, as well as FIGS. 9 and 10, each of these assemblies will be described in greater detail. The test piece control assembly 372 is employed in connection with controlling movement of the test piece 332 having a number of sensing units 100 that may have an analyte of interest. The test piece control assembly 372 includes a motor 388 that is held or supported by a motor mount 392. Operation of the motor 388 including providing and removing power thereto is accomplished using a motor controller 396 that communicates with the digital controller 344. When it is appropriate to move the test piece 332, the digital controller 344 generates the necessary signal for receipt by the motor controller 396 in order to generate a suitable signal for the motor 388. The output of the motor 388 is connected to a first gear 400 that rotates when the motor 388 is powered. The first gear 400 operatively engages the second gear 404. The two gears 400, 404 are at right angles to each other to contribute to the compact size of the instrument 300. Rotation of the first gear 400 causes the second gear 404 to also rotate. The second gear 404 is connected to a drive shaft 408 having a first collar 412 adjacent to the second gear 404 and a first bushing 416 spaced from the collar 412 along the drive shaft 408. First and second support arms 420, 424 receive and support the drive shaft 408. Between the support arms 420, 424, the shaft 408 traverses a test piece path 428 defined in the mounting plate 384. The first and second support arms 420, 424 are held to the mounting plate 384 on opposite sides of the test piece path 428. Inwardly adjacent to each of the two support arms 420, 424 is first drive wheel 432 and second drive wheel 436, respectively. Each of these two drive wheels 432, 436 is toothed or otherwise configured to satisfactorily engage edges or other portions of the test piece 332. Each of the two drive wheels 432, 436, through engagement with the drive shaft 408, rotates when the drive shaft 408 is driven or rotated to thereby cause the test piece 332 to move along the test piece path 428. To complete the discussion of the elements supporting the drive shaft 408, a second bushing 440 is provided about the shaft 408 adjacent to the second drive wheel 436 and a second collar 444 is disposed about the drive shaft 408 on the opposite side of the second support arm 424. The test piece control assembly 372, as seen in FIG. 4, also includes a back plate 448 having an acceptor opening 452 oriented with the receiver slot 328 formed in the end wall 324 of the lower containing unit 308 in order to receive and guide the test piece 332 along the test piece path 428.

With regard to positioning the test piece 332 at a desired position for a particular sensing unit 100 to be analyzed, the reader assembly 376 is utilized. The reader assembly 376 reads or obtains information using the indicia 334 on the test piece 332. This obtained data is sent to the digital controller 344, which analyzes such information in controlling the application of power to the motor 388. As seen in FIGS. 12 and 13, the reader assembly 376 includes a reader element 460 that is precisely and accurately positioned along the test piece path 428 to read indicia 334 on the test piece 332. The position of the reader element 460 is precisely positioned relative to certain elements of the light beam assembly 380, as will be understood more fully when a more detailed description of the light beam assembly 380 is provided. The reader element 460 communicates its output to processing circuitry 464 of the controller assembly 340, as illustrated in FIG. 9. The processing circuitry 464 processes the signal received from the reader element 460 to output a reader signal, including providing desired amplification, filtering to obtain the proper frequency for the signal and removing unwanted noise from the signal. When a modulated light source is utilized, filtering that enhances the ability to differentiate the desired signal from an unwanted DC level of noise is provided. In such a case, such filtering can include the use of Fourier transform techniques that are useful in extracting the DC noise portion from the input signal, then applying an electronic filter and subsequently integrating the resultant signal to obtain the desired, detected signal. After such processing, the processed reader signal is applied to a decoder 468. In the case of reading a bar code, the decoder 468 includes logic for deciphering or otherwise analyzing the signal input thereto in order to generate a digital signal that is indicative of the bar code currently read by the reader element 460. This digital or decoded signal is applied to a serial interface 472 that communicates with the digital controller 344 to thereby provide test piece 332 position information to the digital controller 344.

Returning to FIG. 12, the reader assembly 376 also includes a reader mount 476 having a hole for receiving and tightly engaging the reader element 460. The reader mount 476 is adjustable relative to the test piece path 428 in order to properly align it relative to the test piece path 428. In that regard, the reader assembly 376 also includes an adjusting element 480 located in an adjusting slot 484 whereby the reader mount 476 can be variably located relative to a reader support 488 that is fixably held to the mounting plate 384 adjacent to the test piece path 428.

The light beam assembly 380 also has elements that must be accurately and precisely located relative to the test piece path 428. The light beam assembly 380 provides a light beam that is used in illuminating the sensor containing the analyte of interest, when present, on the particular sensing unit 100 when the test piece 332 is controllably stopped along the test piece path 428 in order to enable the light beam to strike and reflect from the sensing unit 100. In the embodiment of FIGS. 9, 10, 12 and 13, the light beam assembly 380 includes a laser module 496 that provides a source of monochromatic light, although a non-laser source of generated light is feasible. The monochromatic light source may include properly filtered white light, a light emitting diode (LED) or a laser diode. The application of power and the control associated with the light beam outputted by the laser module 496 is provided using the digital controller 344 and a laser regulator 500, which communicates with the digital controller 344. As illustrated in FIGS. 7 and 8, the laser module 496 is supported in an optics mount 504. In the embodiment of FIG. 8, the light beam assembly 380 also includes an adjustable or rotatable linear polarizer 508 for desirably preparing the polarization state of the light beam that is to be incident upon the sensing unit 100 after passing through a polarizer plate 512. More specifically, the linear polarizer 508 is orientated to output only the "s" component or "s" polarization of the light it receives while essentially eliminating or minimizing the "p" component or p-polarization of the light it receives. In another embodiment, a wave plate or compensator is also used in combination with the polarizer 508 prior to the light striking the sensing unit 100 in order to assist in achieving the desired polarized state of the light. In other embodiments, circular or elliptical states of polarized light are obtained and utilized.

The incident linearly polarized light from the polarizer plate 512 is directed to the particular sensing unit 100. The incident light strikes a small area or point on the sensing unit including the analyte of interest, when present. The reflected light includes useful information in connection with determining a change in mass when the specific analyte of interest is present. The light beam assembly 380 also includes a detection assembly 520 that is properly positioned and aligned to receive such reflected light. As long as metal reflectors or materials that have a large imaginary component (e.g., greater than 0.03) of index of refraction are not being used as part of the sensing unit 100, mostly linearly polarized light (s-polarization only) will leave the sensing unit 100 after reflection.

In other embodiments, the light beam assembly 380 is configured to result in only p-polarized light after reflection. An elliptical state of the polarized light can also be achieved in which the elliptical polarized light strikes the sensing unit 100 and the resulting polarized state of reflected light is also elliptical. Alternatively, circular polarized light may be utilized. However, the circular polarization may undergo an interaction at the sensing unit 100 that changes the polarized state of the reflected light to be slightly elliptical.

The detection assembly 520 includes a detector polarizer 528 that removes, extinguishes, filters or absorbs the linearly polarized light that it receives. In another embodiment, a wave or compensator plate may be optionally used with the polarizer 528. Such a component assists in filtering the reflected state of polarized light of any small component of p- or s-polarized light provided in the reflection from the sensing unit 100. It is possible that the composition of the sensing unit 100 may cause some ellipticity to be present in the reflected light and/or that the ellipticity is caused by slight imperfections or small misalignments of the polarizing components. After the foregoing optical processing, the only signal produced, in view of the removal of the linearly polarized light by the detector polarizer 528, will be due to an increase or decrease in the mass of the sensing unit 100. It has been observed that this arrangement decreases the sensitivity to small increases in sensing unit mass changes, with the sensitivity being mainly due to the use of only s-polarized light. On the other hand, a decrease in sensitivity is experienced when other than p- or s-polarized light enters the detector polarizer 528. If any p-polarized light were present, there would be a lower signal-to-noise ratio, which means less sensitivity to small mass changes. More particularly, if the imaginary component of the index of refraction of the sensing unit 100 is at least 0.05, then the light leaving the sensing unit will be elliptically polarized. Elliptical polarization has both "s" and "p" components present. When both of the components are present, the light cannot be extinguished by the detector polarizer 528. In the embodiment being described, the s-polarized light is extinguished and the p-polarized light would continue along the optical detection path. This p-polarized light constitutes optical noise and decreases the sensitivity of the instrument.

In the embodiment of FIGS. 12 and 13, the detection assembly 520 also includes a compensator wave plate 524 that is optically positioned between the sensing unit 100 and the detector polarizer 528. The compensator wave plate 524, typically a quarter-wave plate, allows elliptically polarized light that might leave the sensing unit 100 to be converted to plane or linearly polarized light having only the "s" component. When linearly polarized light is present, it can then be extinguished by the detector polarizer 528 prior to detection of any light signal that might be generated due to a mass or thickness change in the sensing unit 100.

It should be appreciated that the wave or compensator plate previously discussed can be used on either side of the reflection from the sensing unit 100. The choice of retardation in the compensator plate is based on what is required to optimize the signal-to-noise ratio of the particular optical component configuration. Depending upon such circumstances, a ⅛, ¼, ½ or other wave retardation can be selected.

In another embodiment, instead of s-polarized light being applied to the detector polarizer 528 to be extinguished by it, only p-polarized light is produced and applied to the detector, with the "s" component polarizer 528 already having been essentially eliminated or minimized by the polarizer elements that output the incident light to the sensing unit 100.

The output of the detector polarizer 528 is applied to a detector unit 532 that includes, for example, a photodiode for use in detecting or measuring the intensity of the light received by it. The intensity of the light detected relates to the change in mass due to the analyte of interest when it is present with the sensing unit 100 as will be described further herein. As seen in FIG. 10, the detector unit 532 communicates with detector processing circuitry 536 of the controller assembly 340 (FIG. 9). The detector processing circuitry 536 processes the analog signal from the light detector unit 532 including appropriate amplification and signal filtering including, as previously noted, the use of Fourier transform filtering. The output of the detector processing circuitry 536 is applied to an analog-to-digital converter (ADC) 540 for converting the analog signal to a digital signal acceptable to the digital controller 344. This digitized light signal represents the light intensity of the reflected light from the sensing unit 100, including analyte of interest, when present. This digital light signal is then analyzed in connection with making a determination regarding the presence or absence of the analyte of interest with the particular sensing unit 100 being tested.

In another embodiment, instead of a photodiode type of detection, an imaging detector, such as a video type, charge coupled device (CCD) and so forth, can be used to capture intensity change of the sensing unit as well as an image of the sensing unit being tested. This type of image inspection would be equivalent to scanning the sensing unit with a 0.012 mm laser beam. Using data from about 0.012 mm section of a sensing unit, different types of digital analysis can be applied to determine the amount of material captured. For instance, if some non-specific material were also captured with the analyte of interest, and they were larger in size or had different polarization properties, their presence could be detected when their size is in some reasonable relation to the 0.012 mm detection resolution, or the polarization property were high enough above general noise. This means that these areas are potentially selectable and can be eliminated from the overall signal.

In another embodiment, an optical apparatus involved with the control of the incident light and collection of reflected light utilizes two detectors and no compensator plate. Such a configuration does not contain any moving or adjustable components like polarizers or compensator plates. In accordance with this configuration, light will reflect from the sensing unit at the proper or desired angle other than 0°, 90° or Brewster's angle. After leaving the sensing unit, the light will again reflect from a detector or silicon substrate that is positioned at or near Brewster's angle. This reflection will eliminate all of the p-polarized light and leave only s-polarized light. The use of a silicon detector for the reflected light after the sensing unit is beneficial since a reading of the amount of p-polarized light can be obtained, which may prove valuable in making precise calculations regarding the material on the surface of the sensing unit. The remainder of the reflected light will be collected by a final or another detector, comparable to those previously discussed. The final value of the s-polarization light that was collected can be compared to s-polarization light that is collected from a sensing unit that has no analyte of interest. An instrument that includes this optical apparatus can have three outputs, s-polarized light, p-polarized light and the ratio of the p-to-s amplitudes. This ratio is a common ellipsometric calculation and can assist calculating other values of interest.

Figure 14:
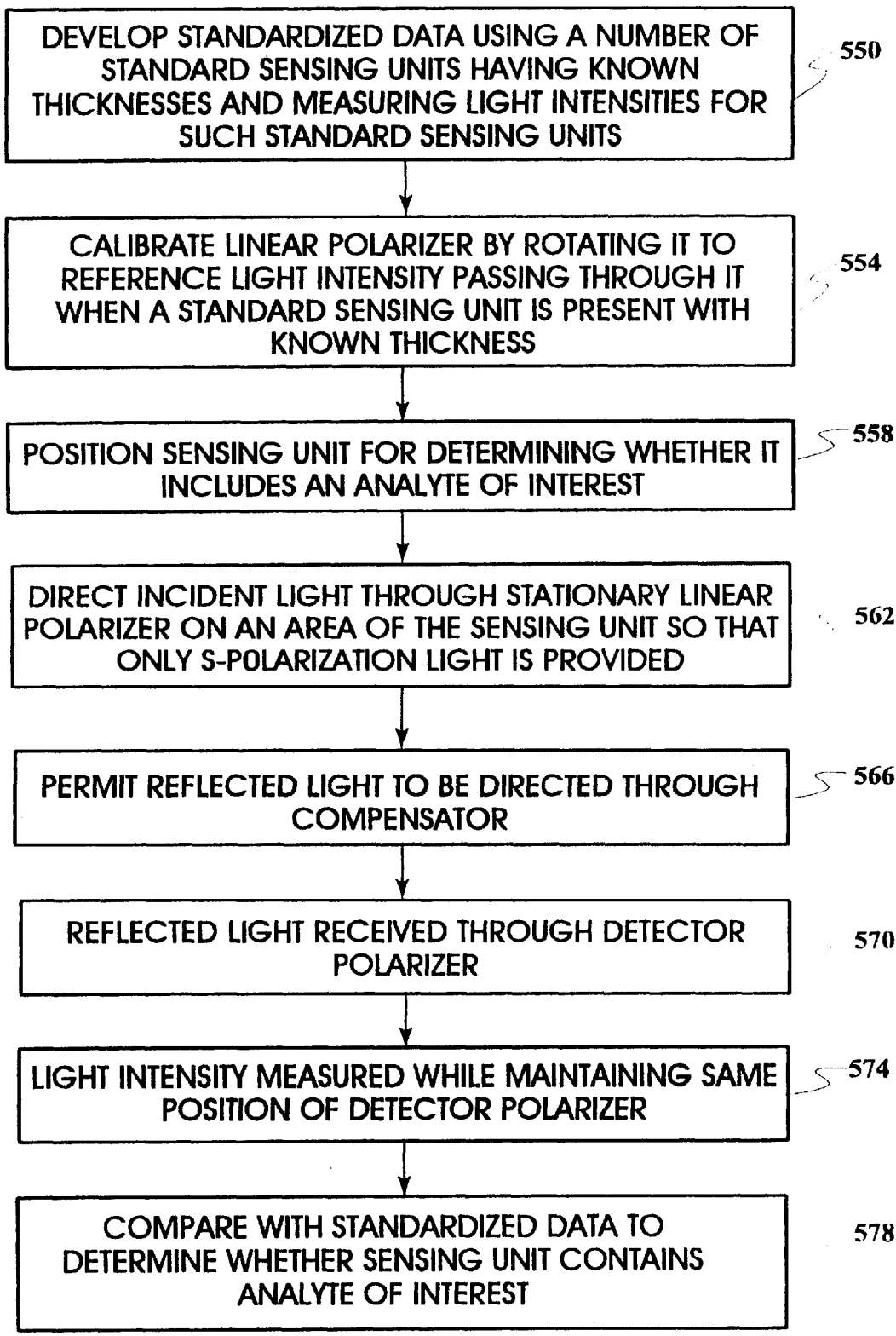
FIG. 14 is a flow diagram setting out major steps related to the operation of the instrument using one embodiment of a light beam assembly.

Additional details of the embodiment of FIGS. 12 and 13 associated with the analysis are next described with reference to the flow diagram of FIG. 14. In accordance with the method of this embodiment, unlike known prior art, only one polarized light component is received at the detector polarizer 528, such as the s-polarization, while the linear polarizer elements 508, 512 and the detector polarizer 528 remain stationary in their same position or orientation that each had when the incident light is first generated and then directed to the particular sensing unit 100 that is being tested.

With respect to using the determined light intensity from the sensing unit 100 in order to detect whether or not the analyte of interest is present, the present invention relies on previously generated standardized data that may be presented in the form of standardized curves or plots. Such standardized data may also be represented by a number of discrete data points stored in memory that can be interpolated to arrive at any value between such discrete data points. Such data points relate to values of light intensity associated with a number of standardized or accurately measured masses for a number of sensing units that include masses that are intended to correlate with changes in mass to a sensing unit currently being tested when a substance of interest is present. For example, the instrument 300 is used with a standardized sensing unit 100 that includes a mass representative of a mass when an analyte of interest is present. Measurements are conducted using this standardized sensing unit. Data is collected for this particular sensing unit having this first known mass, as well as other sensing units having other known masses. Such known masses are correlated with light intensity values that are obtained. The results of such standardization development include correlated masses and light intensity values, as noted in step 550 of FIG. 14.

With such information or data available, step 554 defines a calibrating step that is conducted prior to performing the detection process associated with a particular sensing unit 100. Specifically, the detector linear polarizer 528 is calibrated by desired rotation thereof to obtain a reference light intensity that passes through it when a known or standard sensing unit is present to reflect light. This reference light intensity may have a zero or substantially zero intensity value. After this calibrating step that involves rotating the detector linear polarizer 528, at step 558, a sensing unit 100 is then properly positioned to receive incident light. At step 562, the incident light is directed to a point or small area on the particular sensing unit 100. Reflected light from this point on the sensing unit 100, including analyte of interest when present, is received through the compensator wave plate 524, in accordance with step 566. At step 570, the reflected linearly polarized light is received through the detector polarizer 528, which is not rotated during this detection process but remains stationary, as recited in step 574. After the intensity of the light is obtained using the light detector unit 532, the detector circuitry 536 and the analog-to-digital circuitry 540, the digital light signal representative of the intensity is applied to the digital controller 344. At step 578, the digital controller 344 including a processor thereof compares the digital light signal with the previously developed data, as noted in the discussion of step 550. Based on a comparison between the previously developed standard data and the obtained light signal, a determination is made as to any change in mass in the sensing unit 100. Based on such a determination, a result can be provided as to whether or not the analyte of interest is present.

The result of this determination can be displayed using the liquid crystal display 352. Additionally or alternatively, such result information, as well as other data, can be supplied or downloaded to an external apparatus, such as a computer system using a serial I/O connection 590 of FIG. 10 that communicates with the serial interface 472 to the digital controller 344. The data associated with the result of each such test can also be stored in the data memory 364 for later access and use.

Figure 15A:
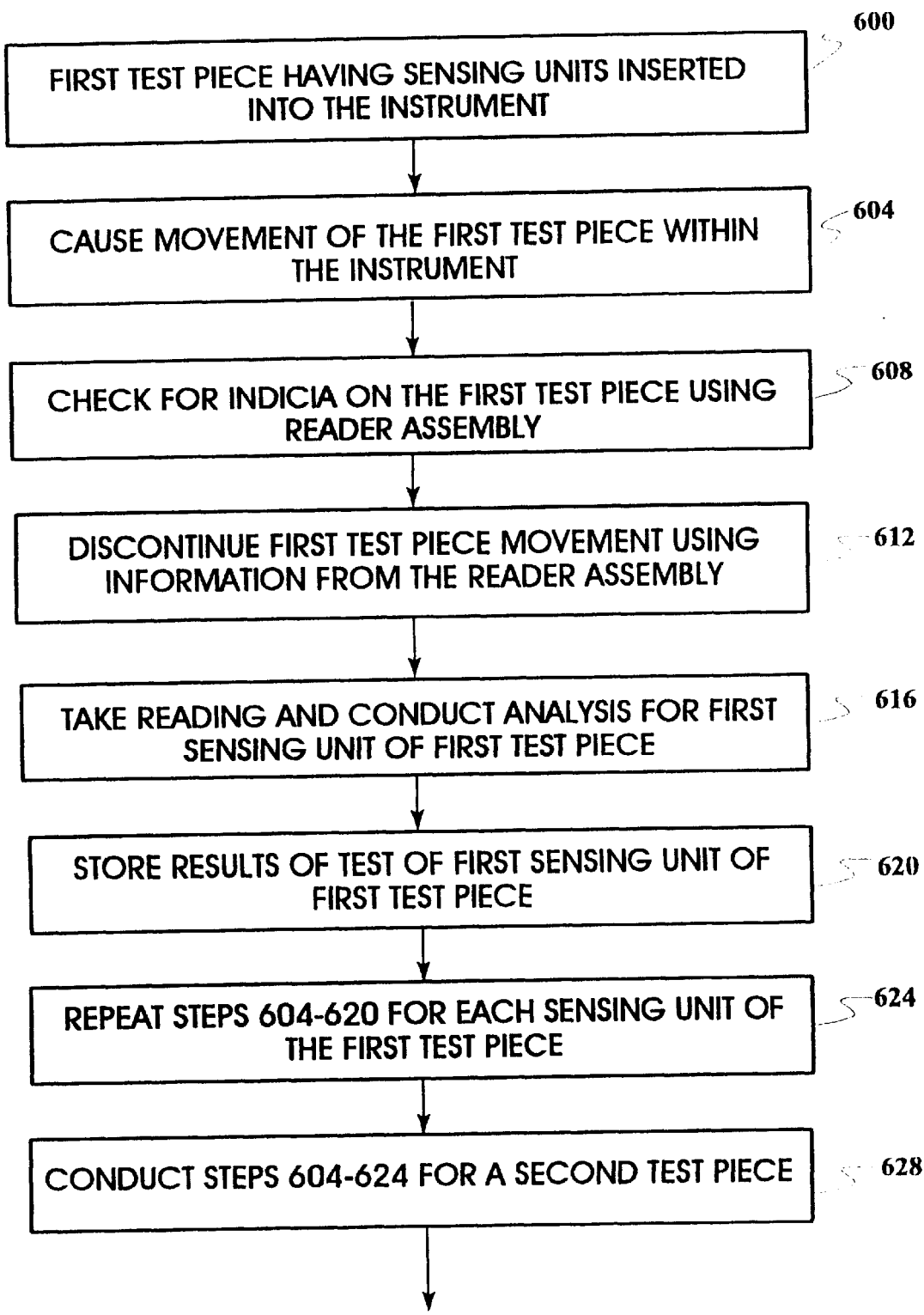
FIGS. 15A-15B are flow diagrams setting out steps related to conducting analyses of a number of sensing units using two test pieces.
Figure 15B:
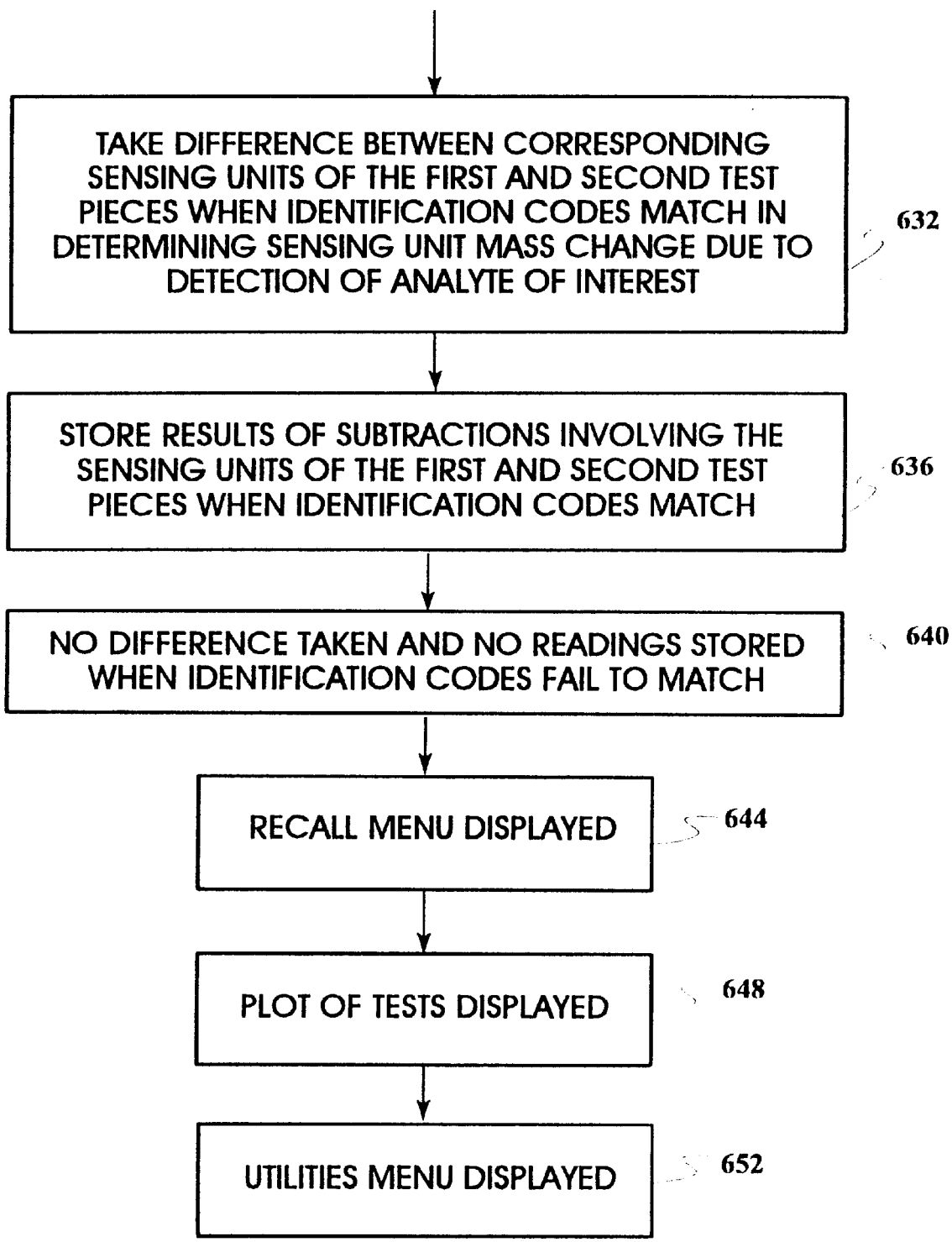
Figure 16:
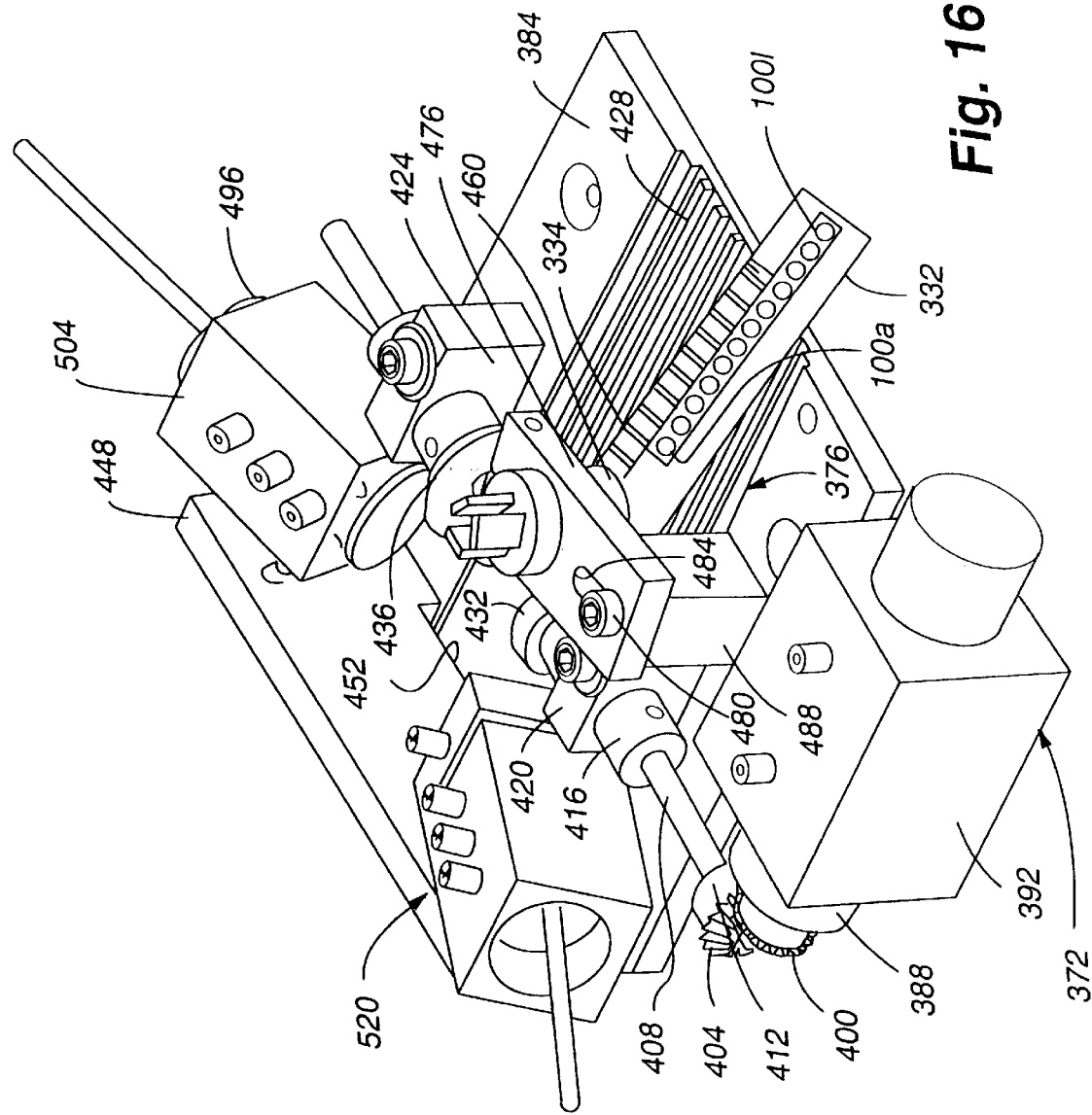
FIG. 16 diagrammatically illustrates a test piece having a number of sensing units in a desired position under control of the instrument of the present invention.

Regarding data that is obtainable in connection with analysis of one or more sensing units 100, a further description is provided with reference to FIGS. 15-16. In accordance with this method, a differential analysis is conducted. More specifically, a difference in results is obtained between related sensing units 100 found on successively tested test pieces. That is, a difference is taken between the results obtained for a first sensing unit, which is being tested for an analyte of interest, and a sensing unit that does not have such an analyte of interest. The first sensing unit is positioned on a first test piece and the second sensing unit is positioned on a second test piece at a corresponding location. The difference that is found is a signal or light intensity due to the analyte of interest when present from the chemical reaction or capture process. These operational steps also differ from known prior art in connection with the use of a controllable motor for automatically positioning each of a number of sensing units on a test piece relative to components that are involved in the detection process.

FIGS. 15A-15B illustrate flow diagrams setting out major steps in conjunction with obtaining results and associated data for a number of sensing units 100 on a first test piece 332 for use in determining whether one or more of them has an analyte of interest. In accordance with step 600 of FIG. 15A, a first test piece 332 having a number of sensing units is positioned for movement relative to the instrument 300. At step 604, the first test piece 332 is moved relative to the instrument 300 along the test piece path 428. A continuous check is made at step 608 for a mark and/or identification code (bar code) or any other indicia on the first test piece indicative of a first sensing unit 100. At step 612, movement of the first test piece 332, under control of the test piece control assembly 372 and the controller assembly 340, is discontinued, based on a determination using the reader assembly 376 that the first sensing unit 100 on the first test piece is properly positioned for analysis, including the obtaining of a reading related to whether or not an analyte of interest is present with this first sensing unit 100. A desired position of the test piece 332 along the test piece path 428 for conducting the test on the first sensing unit 100a is illustrated in FIG. 16. Subsequently, the light beam assembly 380 is activated to take a reading and conduct the analysis for this first sensing unit of the first test piece at step 616. The reading obtained is indicative of the presence or absence of the analyte of interest for this particular sensing unit 100 and at step 620, the results and associated information for this first sensing unit on the first test piece 332 is stored in the data memory 364. In one embodiment of the invention, the data that is stored includes a location number indicative of the position or number of the sensing unit 100 for the first test piece 332, an identification code that identifies the sensing unit, the result of the analysis in terms of a quantitative value obtained using the digital light signal generated using the light beam assembly 380 and subsequent processing circuitry, the date that the analysis was conducted and the time of such analysis In accordance with step 624, steps 604–620 are repeated for each sensing unit 100 that is found with the first test piece 332. Then a second test piece 332 having a corresponding number of sensing units 100 is provided, with each of these not having an analyte of interest. Steps 600–624 are conducted using this second test piece 332 in accordance with step 628. With respect to the results that are obtained using the digital light signal, a difference is taken between corresponding sensing units of the first and second test pieces when there are matching identification codes at step 632 of FIG. 15B. For example, the determined result of the analysis for location 1 of the first test piece is subtracted from the determined result for location 1 of the second test piece when the identification codes match and these two locations correspond to each other. As noted, any sufficient difference is indicative of a mass or thickness change and, concomitantly, an indication that an analyte of interest is present with the sample on the sensing unit 100 that was tested. At step 636, the result of each of the subtractions is saved or stored and, if the result is less than zero, the value 0.0 is stored. At step 640, on the other hand, if it is found that there is a lack of correspondence between the first and second test pieces, no subtraction is taken and no readings are stored.

The program code or software that is useful in implementing the foregoing steps also includes a number of capabilities, which are identified by steps 644–652 of FIG. 15B. At step 644, a recall menu is displayed using the liquid crystal display 352. A number of recall functions are available for implementation. "Recall Last", when invoked or pressed, displays information about the last test that was conducted and the reading taken including displaying identification information, the date and time that the reading was obtained, together with the reading result that, in one embodiment, is displayed in volts. "Recall/Scroll", when invoked or pressed, displays the same results as "Recall Last" and scroll keys are used to enable the user to scroll over and back through all memory locations. "Recall By ID", when invoked or pressed, allows the user to enter the identification code and information is displayed relating to all readings that have that identification code.

At step 648, the user is able to enter a "Plot Request" by which a number of samples of data for a single identification code are displayed. In order to make this request, the desired identification code is entered and an initial number of readings, up to a maximum number, is plotted and displayed. When there are more than the maximum number of readings for the entered ID, the additional or excess samples can also be plotted by pressing an appropriate key on the keypad 316. When there is no match between the requested identification code and available readings, a display is provided to the effect that no such readings are available for that entered identification code.

In accordance with step 652, the program code includes a number of utilities that can be accessed. Display 352 is used to provide the utilities menu or menus. The utilities menu includes "Show System" for displaying current information related to the particular instrument 300 including: the current memory location for the sensing unit under test; the total number of memory locations for the particular instrument; the number of memory locations still available; the current date; the current time; the current identification code; the number of locations that will be read associated with a test piece having the sensing units; the current gain for the detector processing circuitry 536; the current software version and the current hardware version. The utilities menu also includes a "download data" which is used to download all current data stored in the data memory 364. The downloaded data can be received by, for example, a personal computer. The utilities menu also includes the following: "change identification code" by which the user is able to change the current identification number or code to another number or code; a "change gain" by which the user is able to adjust the gain between minimum and maximum values; "change number of locations" by which the user is able to adjust the number of locations on the test piece 332 that will be automatically read; "laser on/off" by which the power to the laser can be separately controlled; and "motor CW/CCW" by which a key is used to turn on the motor 388 and toggle the direction of the motor in connection with confirming the current direction thereof. Numerous other utilities can be provided or implemented depending upon the needs of the user.

Figure 17:
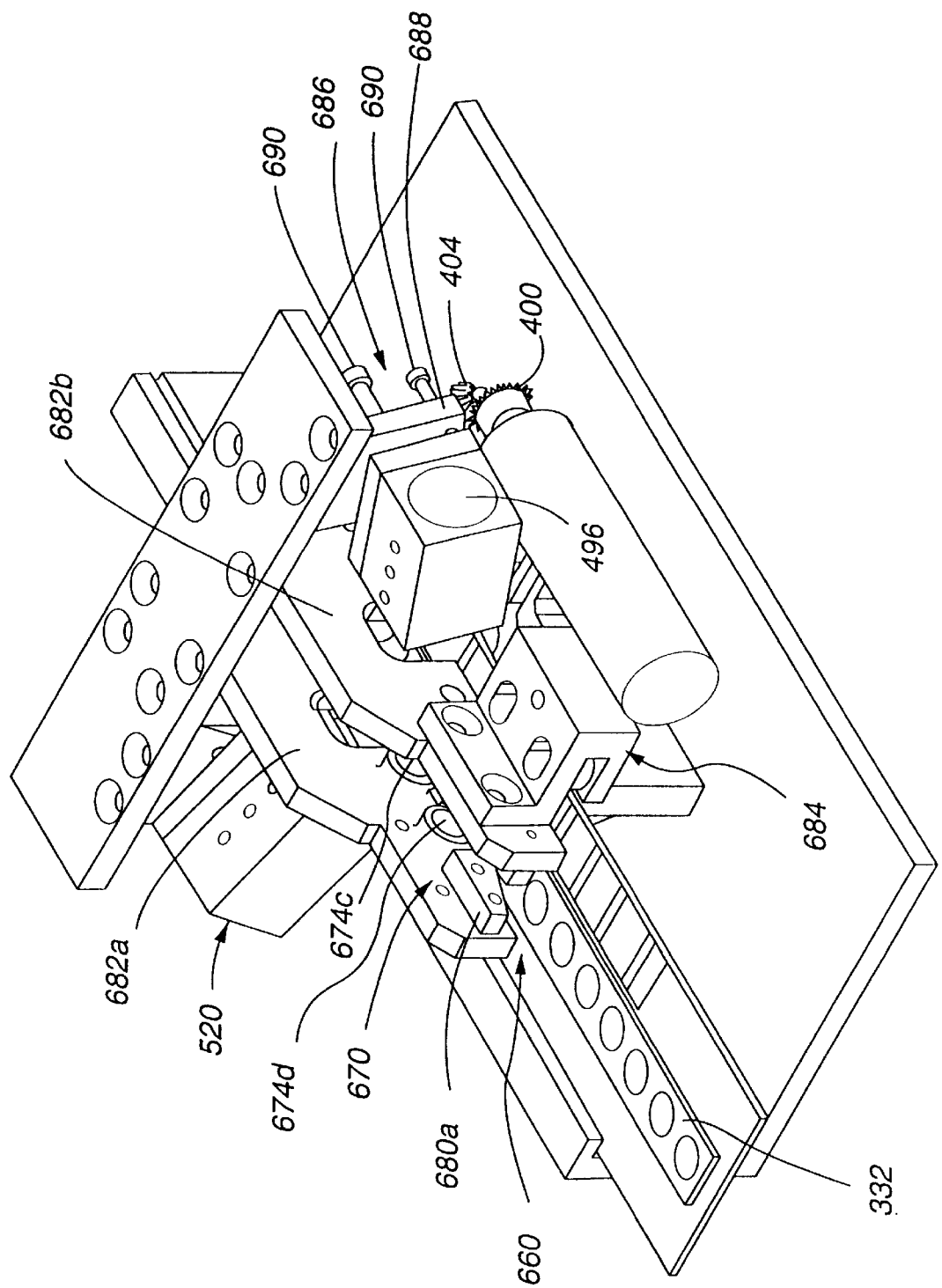
FIG. 17 illustrates another embodiment of an instrument that includes a test piece control assembly of a second embodiment.
Figure 18:
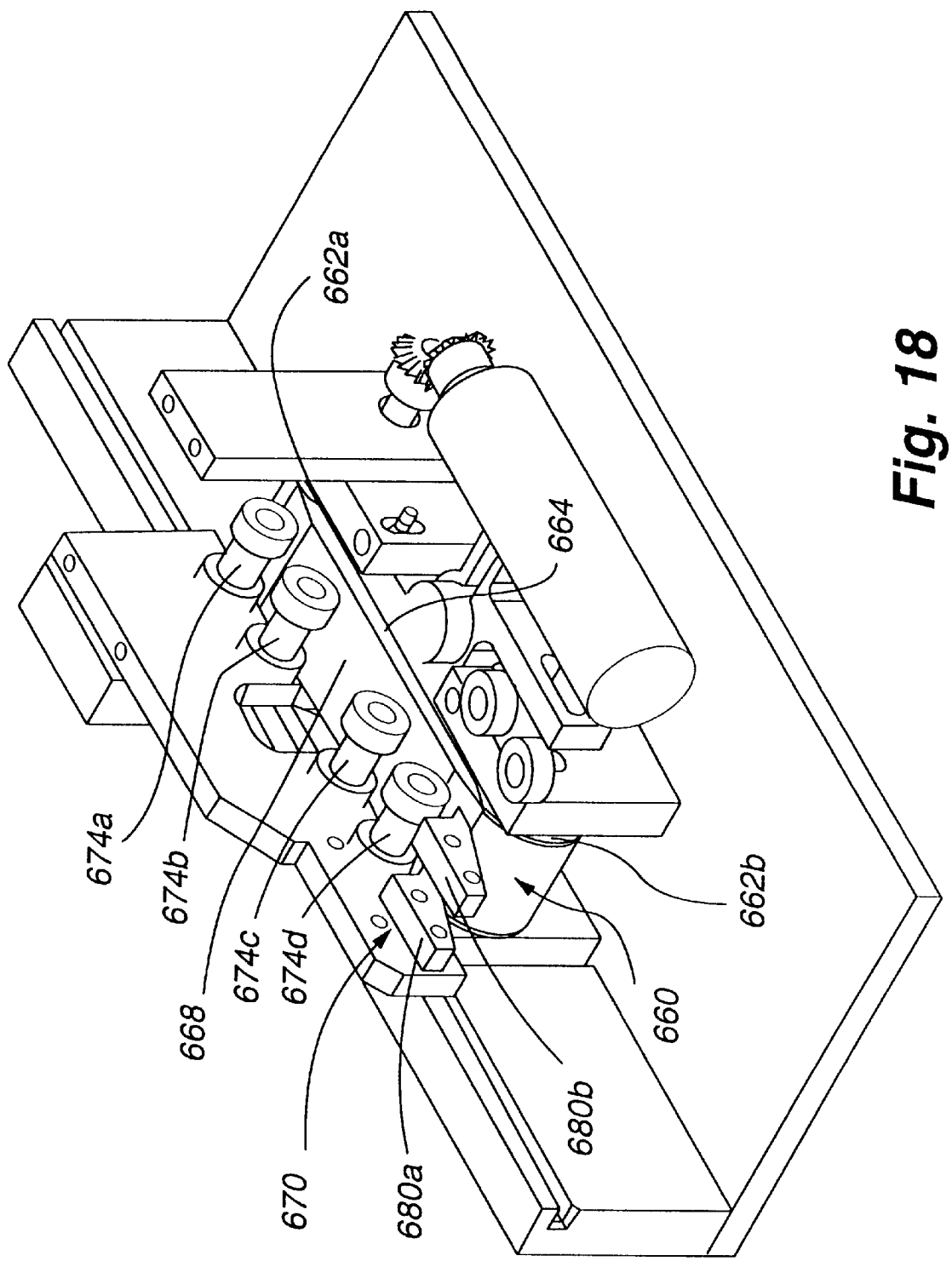
FIG. 18 diagrammatically illustrates another view of the embodiment of FIG. 17 in which further details of the test piece control assembly are shown.
Figure 19:
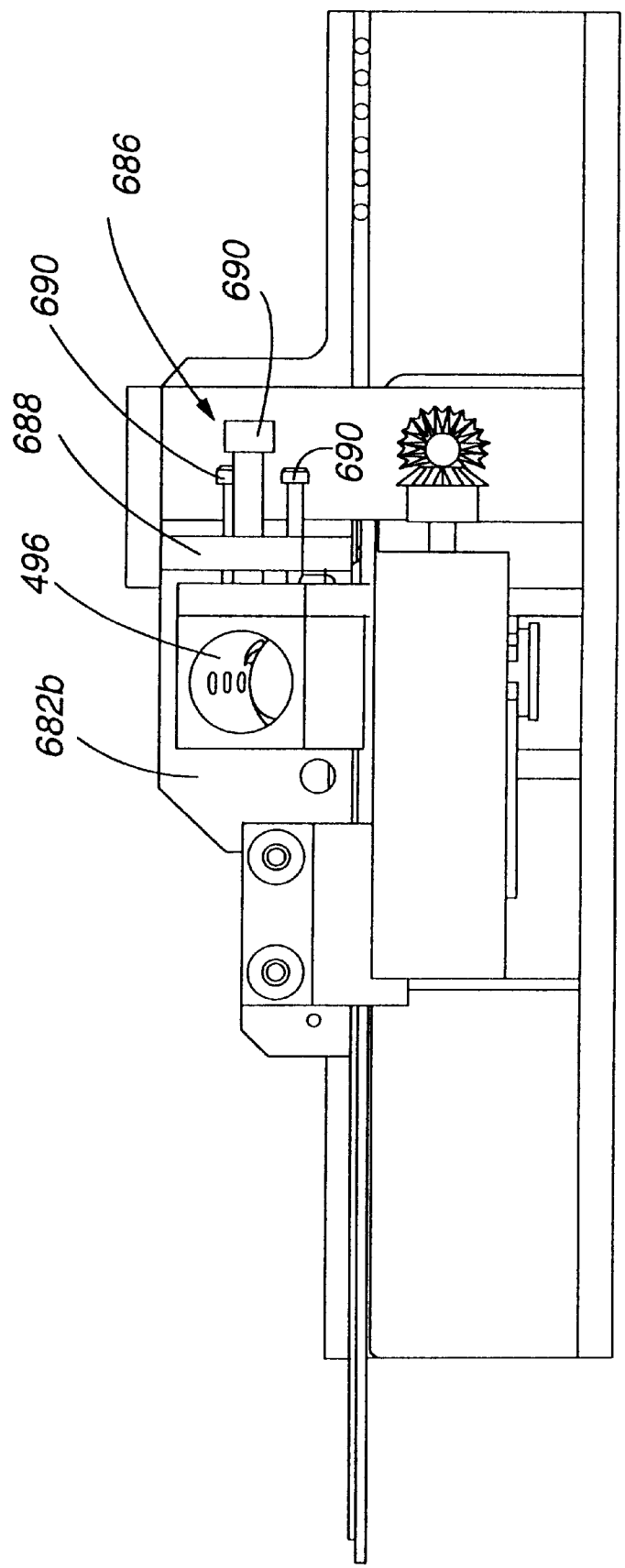
FIG. 19 is a side elevational view of the embodiment of FIGS. 17 and 18.
Figure 20:
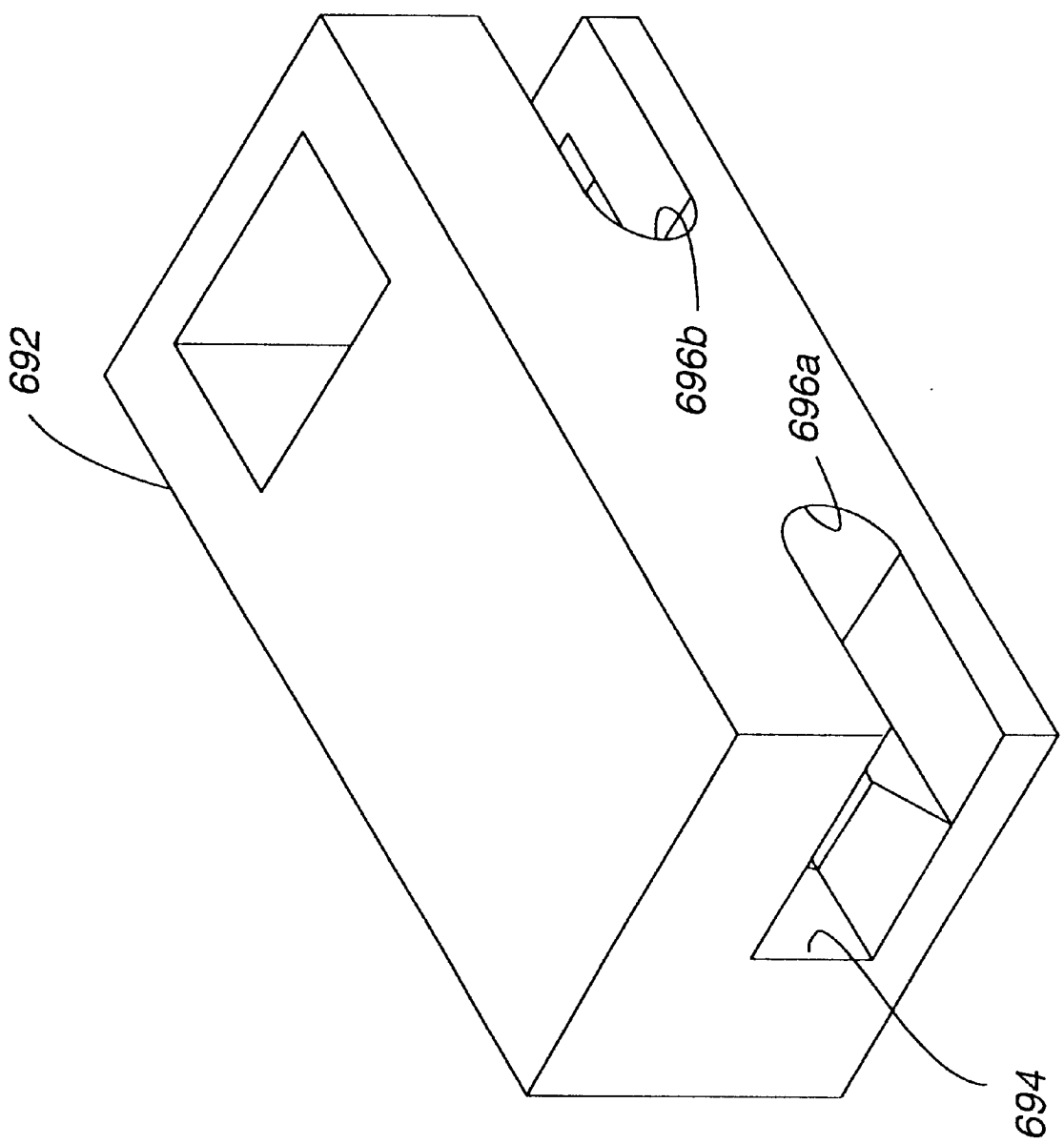
FIG. 20 illustrates a housing for enclosing the embodiment of FIGS. 17–20.

In another embodiment of an instrument primarily characterized by a differently configured test piece control assembly 660, reference is made to FIGS. 17–20. The test piece control assembly 660 for moving the test piece 332 includes first and second drive rollers 662a, 662b. A drive plate 664 is operatively connected to each of the two drive rollers 662a, 662b. A continuous conveyor belt 668 is disposed over the drive rollers 662a, 662b, as well as the drive plate 664. The test piece control assembly 660 also includes a guide assembly 670 that is useful in properly locating or guiding the test piece 332 during its controlled movement along and on top of the conveyor belt 668. In that regard, the drive roller 662a preferably has a biasing mechanism, such as a spring, that causes desired movement in a direction toward the guide assembly 670 to provide suitable positioning of the test piece 332 relative to the guide assembly 670. More specifically, the guide assembly 670 includes a number of guide rollers 674 that are spaced along the length of the conveyor belt 668. In the illustrated embodiment, four such guide rollers 674a–674d are provided. Each of the free ends of the guide rollers 674 engages the edge of the test piece 332. The guide assembly 670 also includes a pair a pawls 680a, 680b that are located adjacent to the entry end of the test piece 332 onto the conveyor belt 668. Each of the two pawls 680a, 680b is desirably positioned for guiding the test piece 332 relative to the top of the conveyor belt 668 as the test piece 332 is received. The test piece control assembly 660 also includes first and second support walls 682a, 682b that are spaced from each other and have the drive rollers 662a, 662b, together with the drive plate 664 and the conveyor belt 668, positioned therebetween. The support wall 682*a* supports the guide rollers 674 and the pawls 680 relative to the conveyor belt 668 and the test piece 332 when it is present in the instrument. As illustrated in FIG. 17, the embodiment of FIGS. 17–20 also includes the support wall adjustment assembly 684. This adjustment assembly 684 is operably connected to the second support wall 682*b* and is used in moving or adjusting the position of the second support wall 682*b* relative to the first support wall 682*a*. Accordingly, the spacing or distance between the two walls 682*a*, 682*b* can be varied in accordance with the width of the test piece 332. In this way, an optimum spacing is achieved that is a function of the width of the test piece 332 so that the test piece 332 can be properly located and guided between the support walls 682*a*, 682*b*. As further denoted in FIG. 17, this embodiment also includes a light beam adjustment assembly 686 that includes an alignment member 688 and a number of fasteners 690 joined thereto. The fasteners 690 are operably connected to the laser module 496 of the light beam assembly 380. Optimum positioning of the laser module 496 and, concomitantly, optimum directing of the light beam outputted therefrom is achieved by adjustment of the position of the laser module 496 using the fasteners 690. By this arrangement, instead of time-consuming and potentially imprecise locating of the laser module 496 in the instrument, adjustment to obtain its optimum position is achieved by movement of the fasteners 690 causing desired movement of the laser module 496 until the optimum position is found. With reference to FIG. 20, a housing 692 for this embodiment is illustrated. The housing 692 includes an angled receiver slot 694 that is geometrically designed to facilitate the entry of a test piece 332 so that it is properly guided for receipt by the test piece control assembly 660. The housing 692 also has a pair of cut-outs 696*a*, 696*b* that permits manual access and movement of the test piece relative to the mechanisms and components located within the housing 692.

ADDITIVE POLARIZATION OPTICS

Other embodiments of the assemblies and components of the instrument 300 can be utilized. With regard to another embodiment of a light beam assembly, reference is made to FIGS. 21 and 22. This embodiment incorporates a "multi-bounce" technique by which the sensing unit 100 being tested is subject to a number of reflected light passes, instead of only one. If an extremely small light beam were used as part of the multi-bounce operation, it could be concluded that the light beam would reflect from a different spot on the sensing unit 100 on each pass of the light. However, the light beam commonly has some finite size, and the area occupied by the analyte of interest, when present, is typically very small so that it is reasonably concluded that the light beam reflects from a small area on the sensing unit and successive reflections will have some overlap with one or more previous small areas that were contacted by the light beam. Such a process of overlapping reflections assists in "averaging out" the total surface area of the sensing unit.

In utilizing the "multi-bounce" technique, the main objective is to produce a sufficient signal above the background noise or other signals to be detected. One bounce or reflection from the sensing unit 100 may not be sufficient to produce such a signal. In order to detect a very thin change in thickness or small change in mass associated with the sensing unit 100 when the analyte of interest is present, a signal produced by one bounce or reflection may not be enough. By causing more reflections on passes of light through the sensing unit and adding each small change of polarization to the previous changes (additive or cumulative polarization per reflection on the sensing unit with analyte of interest when present), then eventually the change in polarization will produce a sufficient intensity change, as represented by the resulting signal, so as to be detected. The multi-bounce embodiment differs from known prior art in generating multiple reflected signals that are at angles other than zero degrees, preferably also different from 90°, to the sensing unit and collecting at least portions of such reflected light signals and analyzing the total collected light signal in determining whether an analyte of interest is present.

Figure 21:
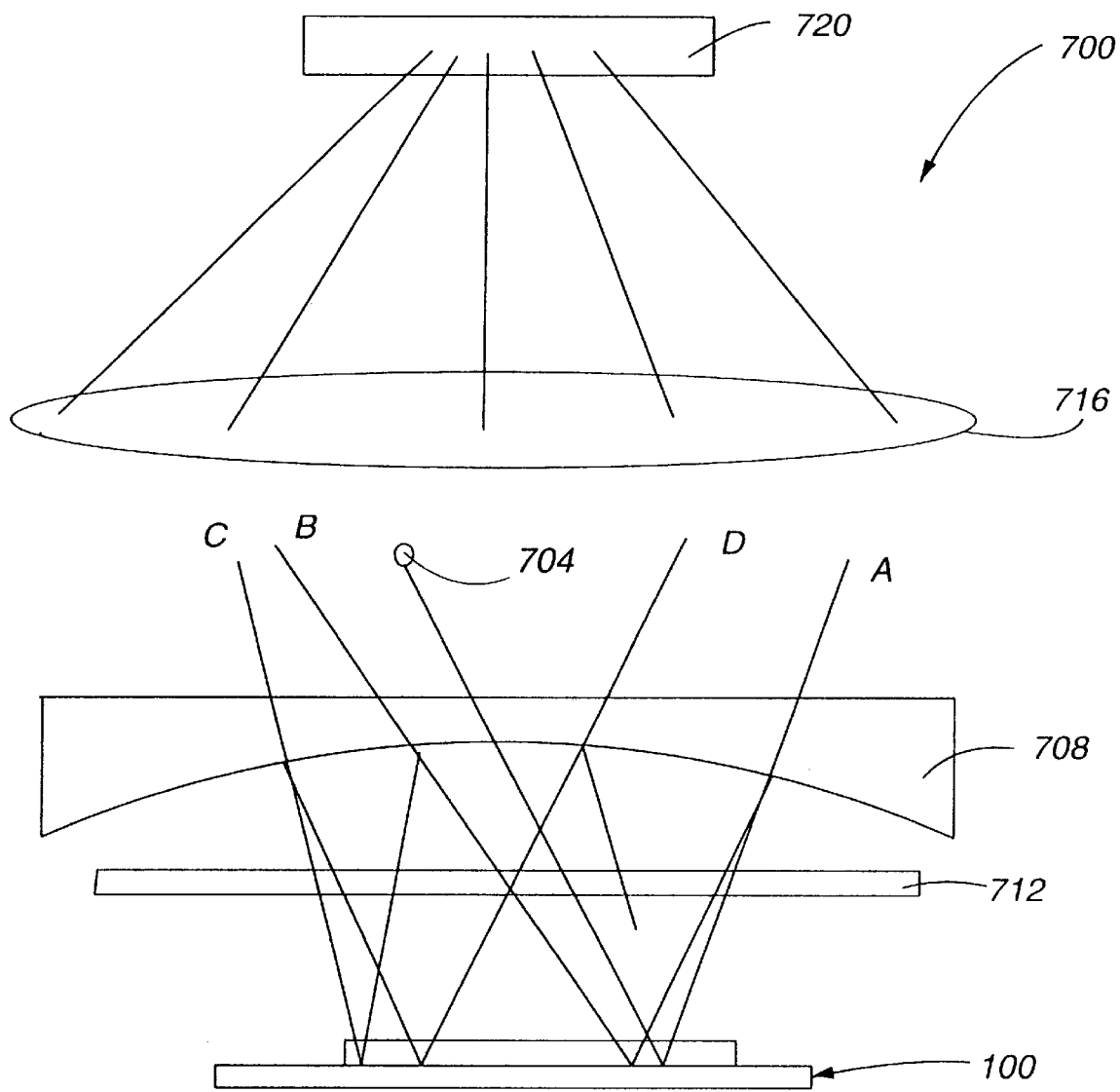
FIG. 21 is a diagrammatic view of another embodiment of a light detection assembly that employs a multi-bounce operation on the same sensing unit in connection with amplifying the reflected light associated with determining whether an analyte of interest is present.

With reference to FIG. 21, an embodiment of a light beam assembly 700 is schematically illustrated that generates multiple reflections and uses partial light transmissions to analyze the intensities of the collection of such partial transmissions. More specifically, the light beam assembly 700 includes a polarized light source 704 that may be monochromatic or some other acceptable source. A curved mirror 708 is properly disposed in the path of the light beam from the source 704. The mirror 708 has optical power and special reflective coatings. A quarter wave retarder or compensator plate 712 is positioned in the path of the light beam that exits the curved mirror 708. The quarter wave retarder plate 712 has an anti-reflective coating on both of its sides. The plate 712 is disposed between the curved mirror 708 and a sensing unit 100. The function of the quarter wave retarder plate 712 is to cause the polarization state that passes through it to be additive after reflection, and not cause a cancellation of the polarization change, as will be explained later herein. The light beam assembly 700 also includes a focusing lens/analyzer plate 716 that is in the path of the partially transmitted light from the curved mirror 708. The focusing lens/analyzer plate 716 can be rotated about its axis in connection with controlling the receipt of the transmitted light from the curved mirror 708. The focusing lens/analyzer plate 716 is suitably positioned to direct the partially transmitted light from it to a detector unit 720, which collects all of the partially transmitted light for subsequent conversion to a light signal representative of the intensities of the collected light. This light signal is analyzed, similar to the embodiment previously described, in connection with determining any change in mass or thickness of the sensing unit 100 due to the presence of an analyte of interest thereon.

With respect to a discussion of the number of "bounces" or reflections, as FIG. 21 illustrates, the polarization light source 704 directs the light beam to the curved mirror 708. Light from the source 704 may or may not pass through the curved mirror 708 and is incident upon the sensing unit 100 at a first point or spot. Light is reflected therefrom and contacts the curved mirror 708 whereby there is a partial transmission of light A together with a further reflection from the curved mirror 708 to a different point on the sensing unit 100. This results in a reflection back to the curved mirror 708, where there is a partial transmission of light B, together with another reflection back to the sensing unit 100. Yet another reflection occurs from the sensing unit 100 at a different point thereon to the curved mirror 708, where partially transmitted light C passes through the curved mirror 708, while additionally reflected light from the curved mirror 708 is directed back to the sensing unit 100 at a different point. At this further different point, another reflection occurs from the sensing unit 100 to the curved mirror 708 and yet another partial transmission light D occurs.

For each of the reflections between the curved mirror 708 and the sensing unit 100, such light passes through the quarter wave retarder plate 712. Each time there is a pass through the plate 712, the polarization state of the light is 90° plus a small change that occurs due to the thickness of the sensing unit 100. The curved mirror 708, on the other hand, has special optical properties regarding polarization and will not introduce any additional polarization and is termed a neutral polarization reflector. Consequently, the only polarization change due to the curved mirror 708 is the 180° change due to the reflection. On the other hand, the quarter wave retarder plate 712 causes the polarization vector to point in the opposite direction from the direction it had when it entered the quarter wave retarder plate 712. After two passes through the retarder plate 712 and one reflection, there is a 360° rotation in the polarization state, together with a small change due to the thickness of the sensing unit 100. In the absence of the retarder plate 712, the vector sum of the polarizations at the sensing unit would be 180° out of phase and would cause a cancellation of the phase change gained on the reflection at the sensing unit. However, by including the one quarter wave retarder plate 712 to the optical path, it produces two 90° polarization changes, each time light passes through first one side thereof and then through the second side thereof. This summing of polarization changes continues for each of the reflections.

Regarding the generation of the partially transmitted light and the multiple reflections of the entering light, this is achieved by the optical power or curvature of the curved mirror surface 708 and the entering angle of incidence of the light beam from the source 704. The reflective properties of the curved mirror 708 also allow for the partial transmission of light through the curved mirror 708 each time reflected light strikes the curved mirror 708.

Figure 22:
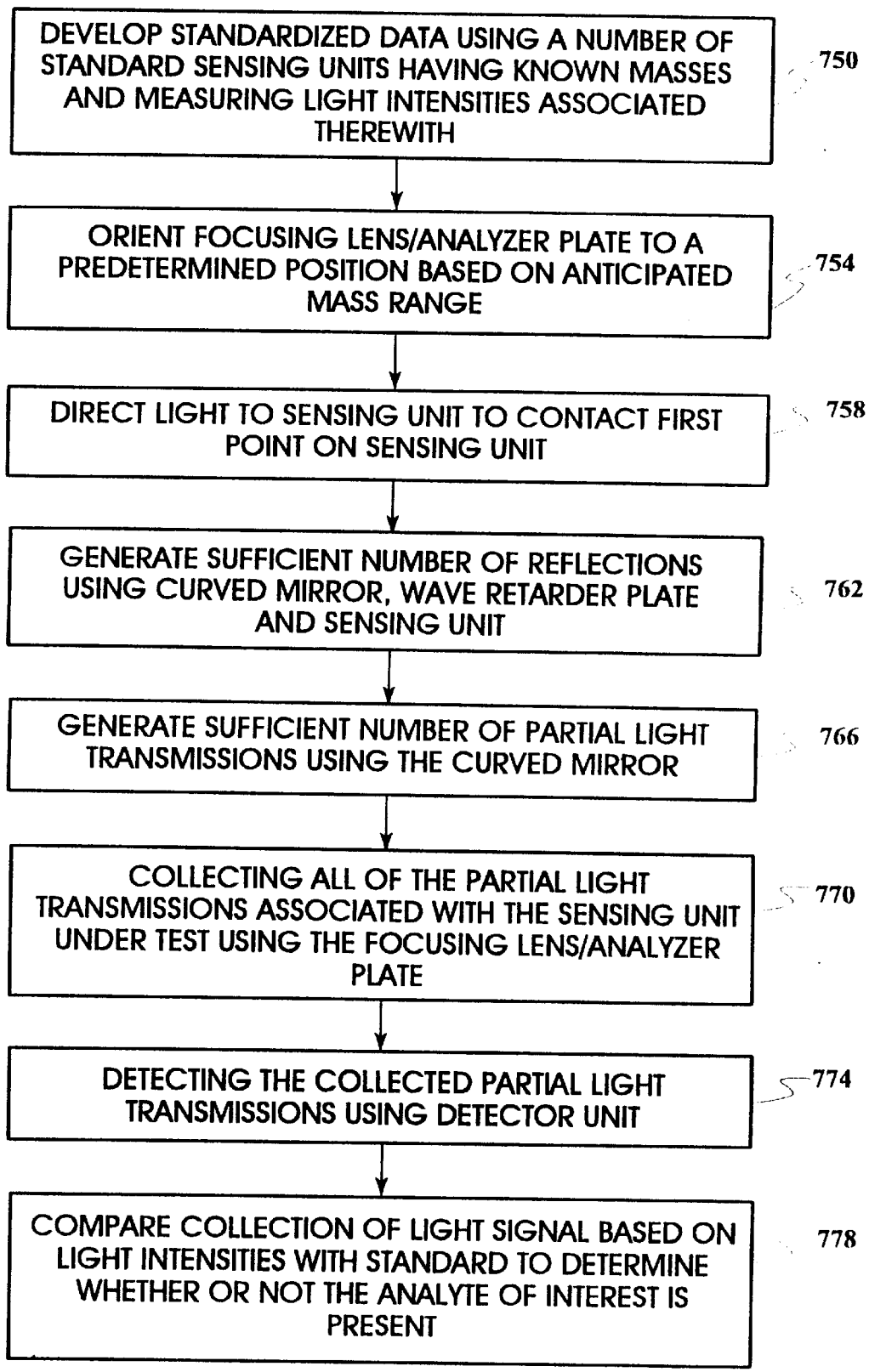
FIG. 22 is a flow diagram setting out major steps related to the operation of the instrument using the embodiment of FIG. 21.

A further description of this embodiment is provided with reference to the flow diagram of FIG. 22 that is directed to major steps related to the obtaining and analyzing of data related to light intensities for determining mass changes. In particular, step 750 of FIG. 22 involves the development of standardized data using a number of standard masses and measuring of light intensities, similar to the step of 550 of FIG. 14 in the previously described embodiment. In accordance with step 754, the focusing lens/analyzer plate 716 must be properly oriented for collection of the numerous partial light transmissions through the curved mirror 708. In that regard, the necessary orientation is previously determined and based on the anticipated masses of the sensing units 100. That is, in connection with testing for a specific analyte of interest, the expected mass range for this analyte of interest was previously determined, and the focusing lens/analyzer 716 is oriented at an angle based on this previous determination. At step 758, power is applied to the light beam source 704, which directs the light beam to the curved mirror 708. A number of reflections are generated, in accordance with step 762 using the sensing unit 100, the quarter wave retarder plate 712 and the curved mirror 708 to thereby produce a larger polarization that is more readily detectable. In that regard, at step 766, a sufficient number of partial light transmissions is generated by which some light from the reflected light on the curved mirror 708 passes therethrough. At step 770, such partial light transmissions are collected using the focusing lens/analyzer plate 716. The numerous partial light transmissions are then detected by the detector unit 720 at step 774. The detector unit 720 uses the intensities of the polarized light to generate a light signal that relates to the mass of the sensing unit 100. At step 778, the value of this sum light signal is compared with the previously determined standard data as part of determining whether or not the analyte of interest is present.

TEST PIECE CONTAINING DEVICE

Figure 23:
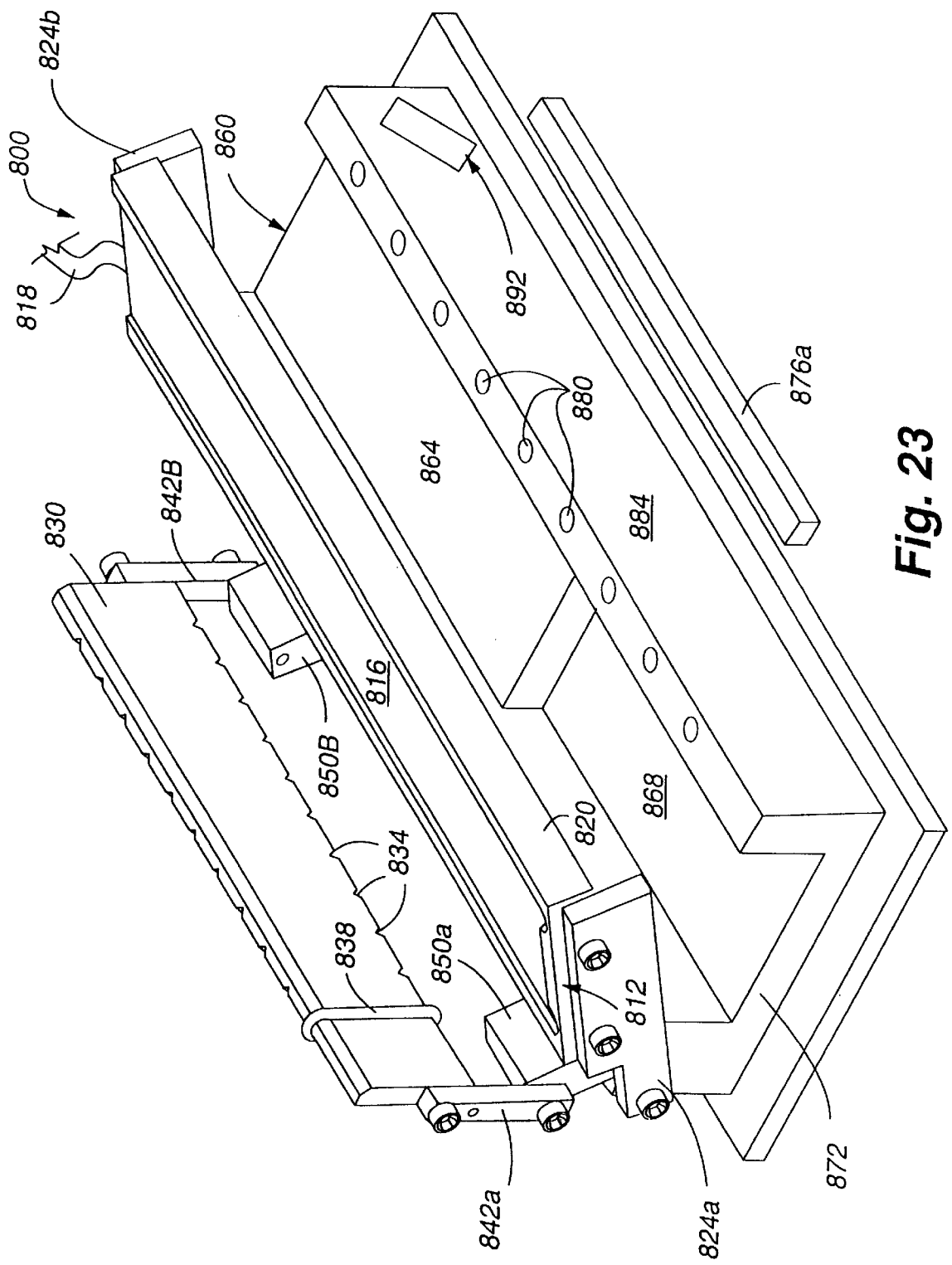
FIG. 23 illustrates a perspective view of a device for containing test pieces that performs a number of functions.
Figure 24:
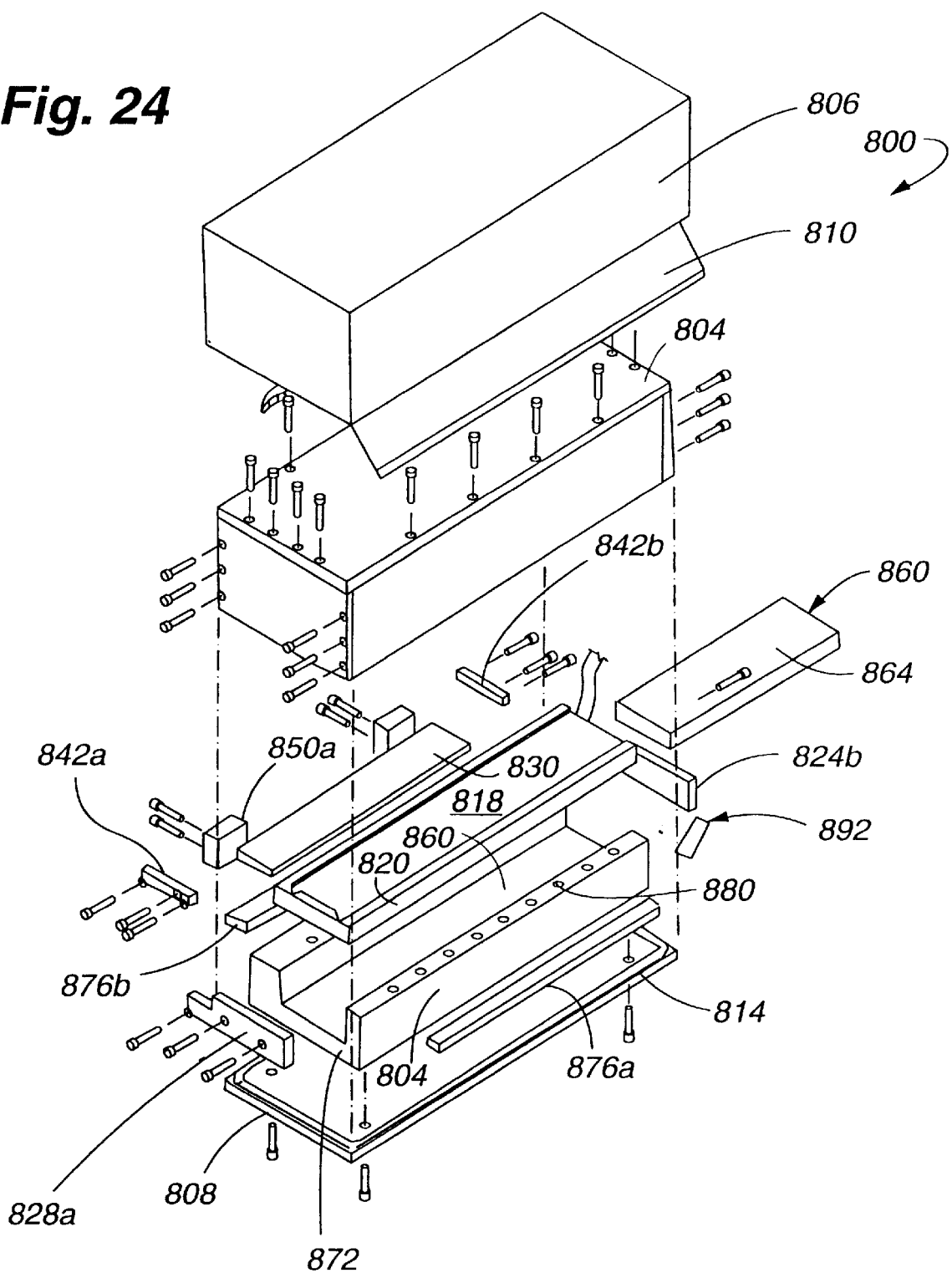
FIG. 24 is an exploded view of the device of FIG. 23.

In one embodiment, with reference to FIGS. 23 and 24, the system also includes device 800 for containing a test piece having a number of sensing units 100 to be tested. Unlike known prior art, the device 800 includes a combination of assemblies and elements that are used, either alone or together, to precisely control heating, humidity, cross-contamination and mixing of materials with or part of sensing units 100. The device 800 includes an enclosure unit 804 (FIG. 15) and a base plate 808 for housing a number of assemblies useful in providing such functions. An insulating cover 806 is preferably provided over the enclosure unit 804 in order to reduce the amount of heat loss to the environment outside of the device 800, which effectively reduces the convection inside of the device 800. When convection is reduced, there is less unwanted evaporation. An inner lid 810 is also provided with the insulating cover 806. The inner lid 810 geometrically influences the convection pattern created by a temperature gradient caused by the heating assembly 812 (higher temperature) and the walls (lower temperature) of the device 800. The inner lid 810 is curved in way that prevents condensation from dripping down onto the sensing units and test piece. The base plate 808 has a sealing ring 814 (FIG. 24) located around its edge which forms a seal between the base plate 808 and the insulating cover 806. This reduces the amount of heat and humidity loss from the device 800 where the base plate 808 and the cover 806 come into contact.

The heating assembly 812 is used to heat the sensing units on the test piece 332 to a desired or predetermined temperature, such as 37 degrees Celsius and maintain that temperature to within at least ±1 degree Celsius. The heating assembly 812 includes a plate sub-assembly 816 that is comprised of a heating element situated between two stainless steel plates. These two plates act as heat reservoirs and are essentially in direct contact with the test piece and, by this arrangement, the heating assembly 812 provides heat to the sensing units by conduction. In order to generate the heat, the plate sub-assembly 816 is powered by a heater controller (not shown) that is electrically connected to the plate sub-assembly 816 by a power cord 818 (FIG. 23). The heating assembly 812 also includes a support frame 820 that surrounds at least some of the periphery of the plate sub-assembly 816. The support frame 820 is connected to lower hinge members 824a, 824b at one end of the support frame 820. The lower hinge members 824a, 824b enable the heating assembly 812 to be pivoted for desired access to the space below the heating assembly 812, as will be understood from a subsequent description of the humidifier assembly of the device 800. Disposed upwardly of the heating assembly 812 is a barrier manifold 830 that is an elongated member having a number of barrier slits 834 that are perpendicular to the elongated plane of the barrier manifold 830. The barrier slits 834 have a sufficient depth to receive barrier members 838 so that portions of the barrier members 838 are held in the barrier slits 834 and other portions of the barrier members 838 extend outwardly from the plane of the barrier member 830. One such barrier member 838 is shown in FIG. 23. The barrier members 838 are spaced a predetermined distance from each other and such spacing is based on the spacing between sensing units on a test piece. That is, the barrier manifold 830 overlies the test piece and each of the sensing units is separated from each of the other sensing units by one or more barrier members 838. In one embodiment, the barrier members 838 include O-rings which contact the body of the test piece without contacting the area where the test is to be taken. Hence, the barrier manifold 830 with barrier members 838 prevents cross-contamination of the sensing units 100. The barrier manifold 830 also allows the sensing units to the washed and dried while in the device 800. The barrier manifold 830 is connected at its ends to upper hinge members 842a, 842b. At their opposite end portions, the upper hinge members 842a, 842b are connected to manifold arms 850a, 850b. This arrangement enables the barrier manifold 830 to be pivoted relative to the plate sub-assembly 816. When a test piece is to be placed in the device 800, the barrier manifold 830 is pivoted away from the plate sub-assembly 816 and the test piece is able to be placed on the plate sub-assembly 816. Then, the barrier manifold 830 is pivoted downwardly over the test piece 332 and provides a slight clamping pressure using the barrier members 838 in order to safeguard against cross-contamination.

The device 800 further includes a humidifier assembly 860 that is comprised of a number of absorbative members for maintaining a relative humidity of 100% within the enclosure unit 804 and the base plate 808 in order to avoid unwanted loss of sensing unit materials due to evaporation. The absorbative members include a main absorbative member 864 that is positioned in a cavity 868 of a base member 872 that is supported on the base plate 808. The main absorbative member 864 has a length that extends for at least a substantial portion of the length of the plate sub-assembly 816 and is positioned essentially directly below this sub-assembly. The main absorbative member 864 is soaked with water prior to its placement in the cavity 868. Two side absorbative members 876a, 876b are also utilized and are located to the side of the main absorbative member 864 adjacent to and on top of a number of wells 880 formed in a wall 884 of the base member 872. The side sponge members 876a, 876b are also soaked with water before placing them in the device 800 next to the wells 880. During use, the side sponge members 876a, 876b draw water from the wells 880 by means of a wicking operation to maintain their soaked or moisture-laden state in order to continue to provide the desired humidity.

The device 800 also includes a mixing assembly 892 (diagrammatically illustrated in FIGS. 23 and 24) which is provided to enhance the mixing of reagents associated with the sensing units 100 to be analyzed. In that regard, and with reference to a single drop of material(s) on the sensing unit 100, the motion and pattern of diffusion has been observed to be a slow descending spiral that varies with the location and orientation of the mixing assembly 892. When this motion within a drop is added to the motion provided by convection due to the drop being heated, there is greater fluid movement and mixing within each drop. In the preferred embodiment, the mixing assembly 892 includes a mechanism for providing oscillatory motion using an offset weight rotating about a fixed axis. This rotation is accomplished by a miniature variable-speed motor. Significantly, as illustrated in FIG. 23, the mixing assembly 892, including the motor and the offset weight, is situated in a compound axis orientation next to the base member 872 along its length. Preferably, the orientation angle is greater than about 10 degrees but less than about 70 degrees relative to the plane of the base plate 808.

In view of the foregoing description, a system is described that includes a number of sub-system components that cooperate with each other in the detection and/or measurement of an analyte of interest using mass change. The system components include a test piece on which a number of sensing units are located that are to be tested in connection with determining whether one or more of them has an analyte of interest. The test piece is dimensioned to be held in a test piece containing device that provides a number of functions in the preparation and care of the test piece with sensing units for subsequent testing. Such functions include precisely controlling the heating, humidifying, avoidance of cross-contamination and mixing of materials that are with or part of the sensing units. The sensing units include an attachment layer that is able to resist delamination of the different layers. The sensing unit may include an attachment layer that is used to immobilize a ligand layer that is receptive to the analyte of interest. The sensing unit may include a tripartite and/or dual element attachment layer that is characterized by an insulating layer located between an upper surface and a lower surface. The insulating layer acts to prevent the transfer of unwanted effects between the lower and upper binding surfaces. The sensing unit may include the dual element attachment layer in which the lower element has an organofunctional silial compound. Mass enhancement systems are preferably utilized that can include a variety of materials such as kinetic-active mass enhancement with one or more desired enzymes associated with the substrate, passive mass enhancement systems in which an existing mass/constant is used and/or a self-assembling amplification system. A further system component is the instrument that is utilized in determining whether or not the analyte of interest is present on a particular sensing unit. The instrument is highly sensitive and able to accurately determine whether an analyte is present Such an instrument may include components for generating and analyzing multiple reflections from the same sensing unit to enhance or amplify the detected signal. The instrument may include optical elements by means of which polarized light having only one component is generated to enhance the detected signal that is indicative of the presence of the analyte of interest.

The foregoing discussion of the invention has been presented for purposes of illustration and description. Further, the description is not intended to limit the invention to the form disclosed herein. Consequently, variations and modifications commensurate with the above teachings, within the skill and knowledge of the relevant art, are within the scope of the present invention. The embodiments discussed hereinabove are further intended to explain the best mode known of practicing the inventions and to enable others skilled in the art to utilize the inventions in such, or in other embodiments and with the various modifications required by their particular application or uses of the inventions. It is intended that the appended claims be construed to include alternative embodiments to the extent permitted by the prior art.

What is claimed is:

1. A sensing system for obtaining information related to sensing units, comprising:

a test piece having a number of sensing units;

a number of indicating means including a first indicating means on said test piece, said first indicating means providing information related to a position of at least one of the sensing units;

a housing having a path wherein said test piece can move along said path of said housing;

a light beam assembly for obtaining information from each sensing unit for use in determining the presence of a specific substance of interest; and controller means located within said housing for causing said test piece to move relative to said housing path, said controller means including a processor and a reader element, said reader element obtaining first information from said test piece using said first indicating means, said first information being input to said processor and said processor providing an output used in controlling movement of said test piece, wherein based on said first information said test piece is positioned relative to said light beam assembly to obtain information related to said one of the sensing units.

2. A system, as claimed in claim 1, wherein:

said first indicating means includes first indicia used in connection with stopping movement of said test piece along said housing path.

3. A system, as claimed in claim 2, wherein:

said first indicia includes an identification code that identifies said one of the sensing units.

4. A system, as claimed in claim 1, wherein:

said housing has a number of walls with a receiver slot in one said walls for receiving said test piece and said controller means comprises a test piece control assembly that includes a motor disposed within said walls of said housing.

5. A system, as claimed in claim 4, further including:

an input unit provided on one of said walls of said housing for inputting information related to the sensing units.

6. A system, as claimed in claim 4, further including:

display means located on one of said walls of said housing for displaying information associated with the sensing units.

7. A system, as claimed in claim 1, further including:

data memory for storing data related to each of the sensing units including identification data, time-related data and data related to whether or not the analyte of interest is present.

8. A system, as claimed in claim 1, further including:

at least a first port communicating with an external computer system by which said external computer system can download software for execution by a processor of said controller means.

9. A system, as claimed in claim 1, wherein:

said processor determines values related to the sensing units and whether or not an analyte of interest is present for each of the sensing units.

10. A system, as claimed in claim 1, wherein:

said first indicating means includes at least one of a mark to indicate a location of said one of the sensing units and a code for identifying said one of the sensing units.

11. A system, as claimed in claim 1, wherein:

said controller means includes a number of electronic components including said processor and in which said electronic components are held on a printed circuit board and in which said printed circuit board is located between said light beam assembly and an input unit for providing input information used by said processor.

12. A system, as claimed in claim 1, wherein:

said light beam assembly includes polarizer means for receiving polarized light having only one component when each sensing unit is tested to determine whether the sensing unit has the analyte of interest and in which said polarizer means remains stationary when said polarized light is being received.

13. A system, as claimed in claim 1, wherein:

said light beam assembly generates a number of reflected light beams having intensities for each of the sensing units, with each of said reflected light beams being produced at an angle different from perpendicular to each of the sensing units.

14. A system, as claimed in claim 13, wherein:

said light beam assembly includes a curved mirror that reflects and transmits light and wave retarder means for providing additive polarization of said reflected light intensities for each of the sensing units to enhance sensitivity for determining the presence of the analyte of interest.

15. An instrument for detecting an analyte of interest, comprising:

first means for supporting a sensing unit to be tested;

second means for locating the sensing unit in a desired position; and third means for determining whether the analyte of interest is present with the sensing unit being tested, said third means including means for generating a number of light reflections from the sensing unit, with each of said light reflections being at an angle other than 0°, said number of reflections including first light portions, second light portions, third light portions and fourth light portions and wherein said first light portions pass through said means for generating, said second light portions are reflected to the sensing unit from said means for generating, said third light portion passes through said means for generating, and said fourth light portions are reflected to the sensing unit from said means for generating, said second light portions include said third and fourth light portions, said third means including collection means for collecting at least some of said first and third light portions and using at least said some of said collected first and third light portions in determining whether the analyte of interest is present.

16. An instrument, as claimed in claim 15, wherein:

said means for generating includes a mirror and a wave retarder plate, said wave retarder plate being disposed in a path of said number of light reflections between the sensing unit and said mirror and wherein said wave retarder plate causes at least said second light portions that pass through it to be additive of polarization change.

17. An instrument, as claimed in claim 16, wherein:

said mirror includes curved portions and in which said mirror has optical power and a reflective coating, with said first and third light portions being transmitted through said mirror.

18. An instrument, as claimed in claim 16, wherein:

said mirror has a reflective coating and said wave retarder plate is a portion of said reflective coating.

19. An instrument, as claimed in claim 15, wherein:

said collection means includes a movable focusing lens/analyzer that is in the path of said first and third light portions.

20. An instrument, as claimed in claim 15, wherein:

at least some of said fourth light portions pass through said means for generating.

21. An instrument for detecting an analyte of interest, comprising:

a test piece for supporting a number of sensing units including a first sensing unit to be tested, said test piece having a number of indicating means including a first indicating means with said first indicating means being different from the number of sensing units and said first indicating means for providing first information related to identification of the first sensing unit;

second means for locating the first sensing unit in a desired position; and third means for determining whether the analyte of interest is present with the first sensing unit, said third means including an optical detecting apparatus that has means for generating polarized light, said third means further including controller means for obtaining said first information using said first indicating means, said controller means includes memory means for storing said first information from said first indicating means and for storing results related to whether the analyte of interest is present with the first sensing unit.

22. An instrument, as claimed in claim 21, wherein:

said polarized light has only one component and said one component includes one of s-polarization and p-polarization.

23. An instrument, as claimed in claim 21, wherein:

said means for generating includes a linear polarizer that receives light prior to the light being incident upon the first sensing unit and said means for extinguishing includes a detector polarizer that receives light reflected from the first sensing unit.

* * * * *